United States Patent [19]

Lesieur et al.

[11] Patent Number: 5,760,071

[45] Date of Patent: Jun. 2, 1998

[54] ARYL(ALKYL)PROPYLAMIDES

[75] Inventors: Daniel Lesieur, Gondecourt; Véronique Leclerc, Lille; Patrick Depreux, Armentieres; Philippe Delagrange, Issy les Moulineaux; Pierre Renard, Versailles, all of France

[73] Assignee: Adir et Compagnie, Courbevoie, France

[21] Appl. No.: 814,283

[22] Filed: Mar. 10, 1997

Related U.S. Application Data

[62] Division of Ser. No. 655,635, May 30, 1996.

[30] Foreign Application Priority Data

May 31, 1995 [FR] France ............ 95 06433

[51] Int. Cl.⁶ ............ A61K 31/405; A61K 31/38; A61K 31/34; A61K 31/17
[52] U.S. Cl. ............ 514/415; 514/443; 514/469; 514/595; 543/507; 549/58; 549/467; 564/56
[58] Field of Search ............ 564/56; 548/507; 549/58, 467; 574/595, 415, 443, 469

[56] References Cited

U.S. PATENT DOCUMENTS

| | | | |
|---|---|---|---|
| 4,992,464 | 2/1991 | Brooks et al. | 514/443 |
| 5,095,031 | 3/1992 | Brooks et al. | 514/419 |
| 5,145,845 | 9/1992 | Johnson et al. | 514/80 |
| 5,464,863 | 11/1995 | Nagamene et al. | 514/443 |
| 5,668,180 | 9/1997 | Lesieur et al. | 514/630 |

OTHER PUBLICATIONS

P. Morgan et al., J. Mol. Endocr. 3, R5–R8 (1989).
Haag and Van Vuuren, Med. Sci. Res. 22, 267–268 (1994).

*Primary Examiner*—Deborah Lambkin
*Attorney, Agent, or Firm*—The Firm of Gordon W. Hueschen

[57] ABSTRACT

The invention relates to a compound selected from those of formula (I):

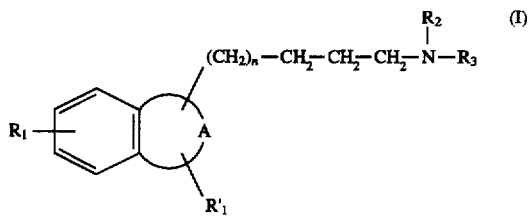

in which A, $R_1$, $R'_1$, $R_2$, $R_3$ and n are as defined in the description, and medicinal product containing the same useful for treating a mammal afflicted with a disorder of the melatoninergic system.

7 Claims, No Drawings

ARYL(ALKYL)PROPYLAMIDES

The present application is a division of Ser. No. 08/655,635, filed May 30, 1996, now allowed.

The invention relates to new aryl(alkyl)propylamides, to a process for preparing them and pharmaceutical compositions containing them.

The invention describes new aryl(alkyl)propylamides which prove to be potent ligands for melatonin receptors.

Benzothiophene compounds which are useful as synthesis intermediates for antihypertensive tricyclic compounds (U.S. Pat. No. 3,714,193) and indole compounds which are used in homotryptamine chemistry (Grandberg I. I. et al Khim. Geterotsikl. Soedin. 1971, 7, pp. 1201–1203 and 1971, 7, pp. 54–57) are known in the prior art.

N-[3-(4-Hydroxy-1-naphthyl)propyl]acetamide and N-[3-(4-benzyloxy-1-naphthyl)-propyl]acetamide compounds are also known in the prior art, as synthesis intermediates (Resch J. F. et al. Bioorg. Med. Chem. Lett. 1991, 1, pp. 519–522).

In the last ten years, many studies have demonstrated the cardinal role of melatonin (5-methoxy-N-acetyltryptamine) in the control of the circadian rhythm and of the endocrine functions, and the melatonin receptors have been characterized and localized.

Apart from their beneficial action on disorders of the circadian rhythm (J. Neurosurg 1985, 63, pp. 321–341) and of sleep (Psychopharmacology, 1990, 100, pp. 222–226), ligands for the melatoninergic system possess advantageous pharmacological properties with respect to the central nervous system, in particular anxiolytic and antipsychotic properties (Neuropharmacology of Pineal Secretions, 1990, 8 (3–4), pp. 264–272) and analgesic properties (Pharmacopsychiat., 1987, 20, pp. 222–223), as well as for the treatment of Parkinson's disease (J. Neurosurg 1985, 63, pp. 321–341) and Alzheimer's disease (Brain Research, 1990, 528, pp. 170–174). Similarly, these compounds have shown activity with respect to some cancers (Melatonin - Clinical Perspectives, Oxford University Press, 1988, pages 164–165), to ovulation (Science 1987, 227, pp. 714–720) and to diabetes (Clinical Endocrinology, 1986, 24, pp. 359–364).

Hence, compounds enabling the melatoninergic system to be affected are excellent medicinal products for the clinician for the treatment of pathologies associated with the melatoninergic system, and in particular those mentioned above.

The invention relates to the compounds of formula (I):

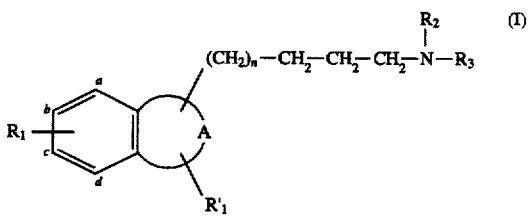

in which:

$R_1$ represents a hydrogen, a hydroxyl, a radical $R_6$ or a group —O—$R_6$. $R_6$ being chosen from alkyl, substituted alkyl, cycloalkyl, substituted cycloalkyl, cycloalkylalkyl, substituted cycloalkylalkyl, alkenyl, alkynyl, cycloalkenyl, phenyl, substituted phenyl, phenylalkyl, substituted phenylalkyl, dicycloalkylalkyl, substituted dicycloalkylalkyl, diphenylalkyl and substituted diphenylalkyl, $R'_1$ represents a hydrogen, a halogen or a group) chosen from:

$R'_6$,
—O—$R'_6$,
—OH,
—CO—$R_7$,
—$CH_2$—$R_7$,
—O—CO—$R_7$, $R'_6$ being chosen from the same meanings as $R_6$, which is as defined above, the radicals $R_6$ and $R'_6$ being identical or different, $R_7$ representing a radical chosen from ($C_1$–$C_5$)alkyl, substituted ($C_1$–$C_5$)alkyl, cycloalkyl, substituted cycloalkyl, cycloalkyl($C_1$–$C_5$)alkyl, substituted cycloalkyl ($C_1$–$C_5$) alkyl, phenyl, substituted phenyl, phenyl($C_1$–$C_5$)alkyl and substituted phenyl ($C_1$–$C_5$)alkyl, A, with the benzene ring to which it is linked, forms a cyclic group chosen from tetrahydronaphthalene, dihydronaphthalene, naphthalene, benzothiophene, 2,3-dihydrobenzothiophene, benzofuran, 2,3-dihydrobenzofuran, indole and indoline, n represents zero, 1, 2 or 3, $R_2$ represents a hydrogen or an alkyl.

$R_3$ represents:

a group of formula ($R_{31}$):

with X representing a sulfur or an oxygen and $R_4$ representing a hydrogen or a radical chosen from alkyl, substituted alkyl, alkenyl, alkynyl, cycloalkyl, substituted cycloalkyl, cycloalkylalkyl and substituted cycloalkylalkyl, or a group of formula ($R_{32}$):

with X' representing a sulfur or an oxygen and $R_5$ representing a hydrogen or an unsubstituted or substituted radical chosen from alkyl, cycloalkyl and cycloalkylalkyl, it not being possible for the compound of formula (I) to represent N-[3-(4-hydroxy-1-naphthyl)propyl]acetamide or N-[3-(4-benzyloxy-1-naphthyl)propyl]acetamide, on the understanding that:

when A, with the benzene ring to which it is linked, forms a benzothiophene group, $R_4$ is an alkyl or vinyl radical, $R_1$ is hydrogen or methyl and $R'_1$ is hydrogen, then n is other than zero, when A, with the benzene ring to which it is linked, forms an indole group, n is equal to zero, $R_2$ represents a hydrogen, $R'_1$ represents a hydrogen or a phenyl, methyl or benzyl radical substituted on the nitrogen of the indole group formed by A, and $R_1$ represents a hydrogen or a methyl group, then $R_4$ cannot be a methyl radical, the term "alkyl" denotes a linear or branched group containing from 1 to 6 carbon atoms, the terms "alkenyl" and "alkynyl" denote linear or branched groups containing from 2 to 6 atoms, the term "cycloalkyl" denotes a group having 3 to 8 carbon atoms, the term "cycloalkenyl" denotes an unsaturated group having 5 to 8 carbon atoms, the term "substituted" associated with the "alkyl" radical means that this radical is substituted with one or more substituents chosen from halogen, hydroxyl and alkoxy, the term "substituted" associated with the cycloalkyl, cycloalkylalkyl and dicycloalkylalkyl radicals means that these radicals are substituted on the cycloalkyl portion with one or more groups chosen from halogen, alkyl, hydroxyl, alkoxy and oxo, and the term "substituted" associated with the phenyl, phenylalkyl, phenyl($C_1$-$C_5$)alkyl and diphenylalkyl radicals means that these radicals are substituted on the phenyl portion with one or more groups chosen from halogen, hydroxyl, alkyl, alkyl substituted with one or more halogens, and alkoxy, their enantiomers and diastereoisomers, and their addition salts with a pharmaceutically acceptable base.

The invention relates especially to the compounds of formula (I) in which, taken separately or together, $R_1$ represents an alkyl, $R_1$ represents an alkoxy, A, with the benzene ring to which it is linked, forms a tetrahydronaphthalene, A, with the benzene ring to which it is linked, forms a naphthalene, A, with the benzene ring to which it is linked, forms a dihydronaphthalene, A, with the benzene ring to which it is linked, forms a benzofuran, A, with the benzene ring to which it is linked, forms a benzothiophene, A, with the benzene ring to which it is linked, forms an indole, $R_2$ represents a hydrogen, $R_2$ represents an alkyl, $R_3$ represents a group $R_{31}$ as defined in the formula (1), $R_3$ represents a group $R_{32}$ as defined in the formula (1), $R_4$ represents a hydrogen atom, $R_4$ represents an alkyl, $R_4$ represents a cycloalkyl, $R_4$ represents an alkenyl, $R_5$ represents a hydrogen, $R_5$ represents an alkyl, $R_5$ represents a cycloalkyl, X represents an oxygen, X represents a sulfur, X' represents an oxygen, X' represents a sulfur, $R'_1$ represents a hydrogen, $R'_1$ represents an alkyl, $R'_1$ represents a phenylalkyl, n represents zero, and n represents 1.

For example, the invention relates to the particular compounds of formula (I) corresponding to the respective formulae (1) to (12):

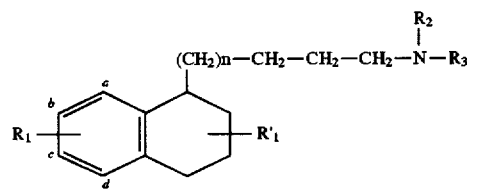

(1)

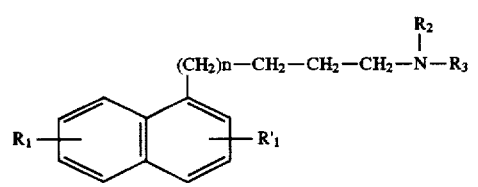

(2)

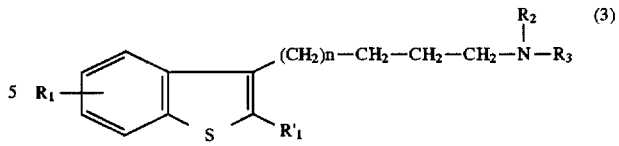

(3)

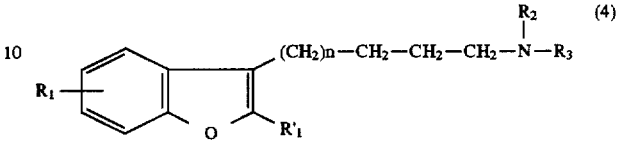

(4)

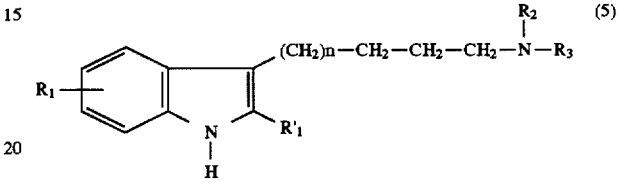

(5)

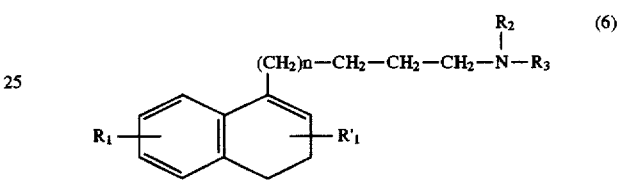

(6)

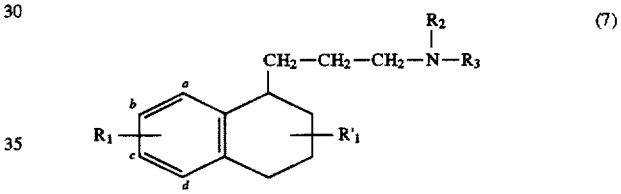

(7)

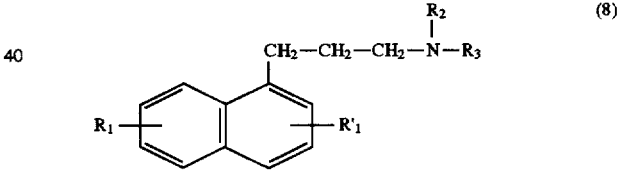

(8)

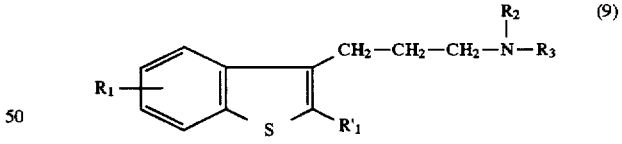

(9)

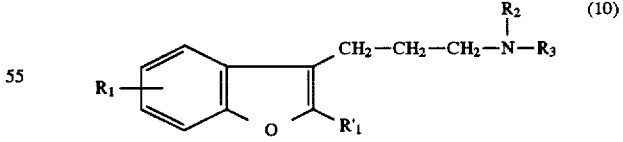

(10)

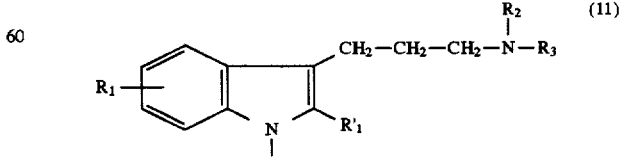

(11)

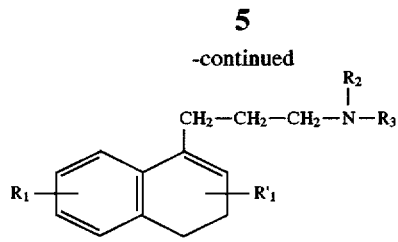

in which $R_1$, $R'_1$, $R_2$, $R_3$ and n are as defined in the formula (I).

The invention relates especially to the compounds of formula (I) in which $R_1$ is:

at position a of the benzene ring,
at position b of the benzene ring,
at position c of the benzene ring,
or at position d of the benzene ring.

For example, the invention relates to the compounds of formula (I) in which $R_1$ is at position b of the benzene ring.

The invention relates especially to the compounds of formula (i) in which $R'_1$ is a hydrogen.

For example, the invention relates to the following compounds:

N-[3-(7-methoxy-1-naphthyl)propyl]acetamide,

N-[3-(7-methoxy-1-naphthyl)propyl]pentanamide,

N-[3-(7-methoxy-1-naphthyl)propyl]cyclopropanecarboxamide,

N-propyl-N'-[3-(7-methoxy-1-naphthyl)propyl]urea.

In particular, the alkyl radicals present in the formula (I) may be chosen from methyl, ethyl, n-propyl, isopropyl, n-butyl, isobutyl, sec-butyl, tert-butyl, pentyl and hexyl, and the skeleton isomers of the pentyl and hexyl radicals;

the alkenyl radicals present in the formula (I) may be chosen from vinyl, allyl, propenyl, butenyl, pentenyl and hexenyl, as well as their isomers according to the position of the double bond;

the alkynyl radicals present in the formula (I) may be chosen from ethynyl, propargyl, butynyl, pentynyl and hexynyl, as well as their isomers according to the position of the triple bond;

the halogens present in the formula (I) may be chosen from bromine, chlorine, fluorine and iodine;

the cycloalkyls present in the formula (I) may be chosen from cyclopropyl, cyclobutyl, cyclopentyl, cyclohexyl, cycloheptyl and cyclooctyl;

the cycloalkenyls present in the formula (I) may be chosen from cyclopropenyl, cyclobutenyl, cyclopentenyl, cyclohexenyl, cycloheptenyl and cyclooctenyl.

Among pharmaceutically acceptable bases which may be used to form an addition salt with the compounds of the invention, sodium, potassium, calcium or aluminum hydroxides, alkali metal or alkaline-earth metal carbonates and organic bases such as triethylamine, benzylamine, diethanolamine, tert-butylamine, dicyclohexylamine and arginine may be mentioned as examples and without implied limitation.

The invention also relates to the process for preparing the compounds of formula (I), wherein a compound of formula (II):

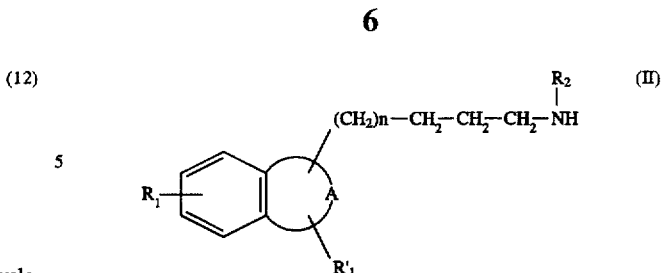

in which $R_1$, $R'_1$, $R_2$, n and A are as defined in the formula (I), is reacted either with a compound of formula (IIIa) or (IIIb):

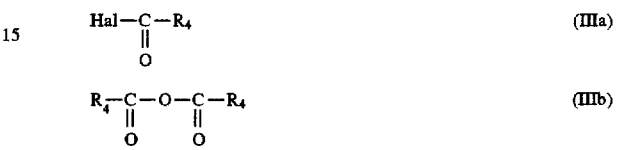

the anhydride of formula (IIIb) being mixed or symmetrical, in which $R_4$ is as defined in the formula (I) and Hal represents a halogen, so as to obtain the compounds of formula (I/a):

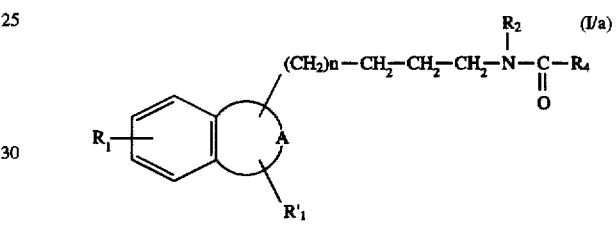

in which $R_1$, $R'_1$, $R_2$, $R_4$, A and n are as defined above, which compounds of formula (I/a) are subjected to a thionating agent, for example Lawesson's reagent, to obtain the compounds of formula (I/a'):

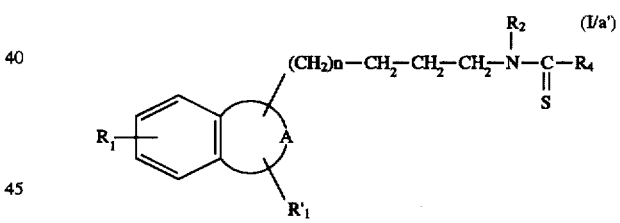

in which $R_1$, $R'_1$, $R_2$, $R_4$, A and n are as defined above, or with a compound of formula (IV):

in which X' and $R_5$ are as defined in the formula (I), so as to obtain the compounds of formula (I/b):

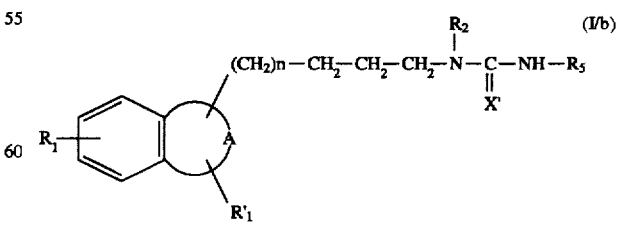

in which $R_1$, $R'_1$, $R_2$, $R_5$, A, n and X' are as defined above, it being possible, if so desired, for the compounds of formulae (I/a), (I/a') and (I/b), which collectively form the compounds of formula (1), to be purified according to one or more purification methods chosen from crystallization, chromatography on silica gel, extraction, filtration and passage over charcoal or through resin, to be separated, where appropriate, in pure form or in the form of a mixture, into their possible enantiomers or diastereoisomers, or to be salified with a pharmaceutically acceptable base.

For example, the invention extends to the process for preparing the compounds of formula (I/c):

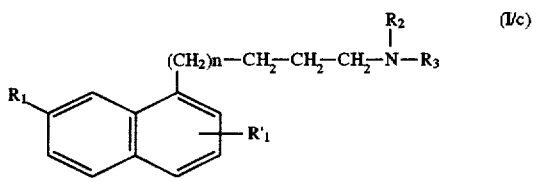

in which $R_1$, $R'_1$, $R_2$, $R_3$ and n are as defined in the formula (1),
wherein:
a compound of formula (II/a):

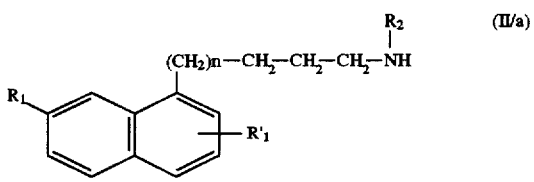

in which $R_1$, $R'_1$, $R_2$ and n are as defined above, is reacted either with a compound of formula (IIa) or (IIIb) as defined above, so as to obtain the compounds of formula (I/d):

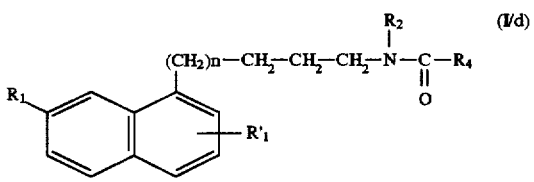

in which n, $R_1$, $R'_1$, $R_2$ and $R_4$ are as defined above, which are then subjected to a thionating agent, for example Lawesson's reagent, to obtain the compounds of formula (I/d'):

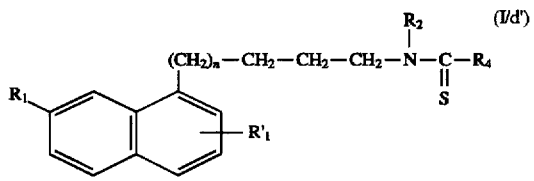

in which n, $R_1$, $R'_1$, $R_2$ and $R_4$ are as defined above, or with a compound of formula (IV) as defined above, so as to obtain the compounds of formula (I/e):

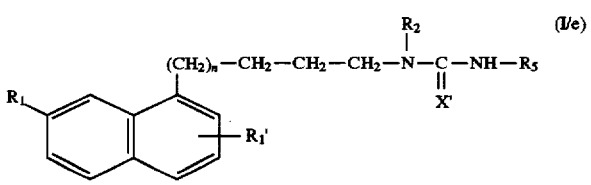

in which n, $R_1$, $R'^1$, $R_2$, $R_5$ and X' are as defined above, the compounds of formulae (I/d), (I/d') and (I/e) collectively forming the compounds of formula (I/c), it being possible, if so desired, for the compounds of formula (I/c)

to be purified according to one or more purification methods chosen from crystallization, chromatography on silica gel, extraction, filtration and passage over charcoal or through resin, to be separated, where appropriate, in pure form or in the form of a mixture, into their possible enantiomers or diastereoisomers, or to be salified with a pharmaceutically acceptable base.

The invention also extends to the process for preparing the compounds of formulae (I/g), (I/h), (I/i) and (I/j), special cases of the compounds of formula (1), wherein a compound of formula (I/f):

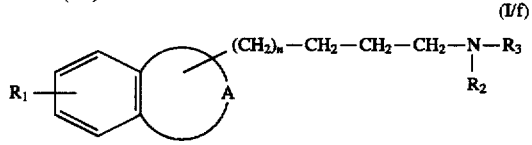

in which n, A, $R_1$, $R_2$ and $R_3$ are as defined in the formula (I), is reacted with a compound of formula (V)

in which Hal is a halogen atom and $R_7$ is as defined in the formula (1), to obtain a compound of formula (I/g):

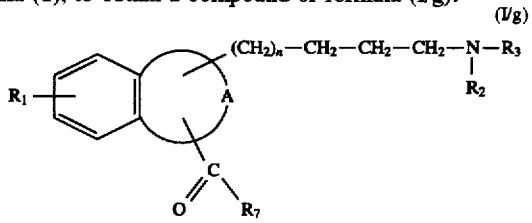

in which n, A, $R_1$, $R_2$, $R_3$ and $R_7$ are as defined above, [5] which may be, if so desired, either subjected to an oxidation by a Baeyer-Villiger reaction to obtain a corresponding compound of formula (I/h):

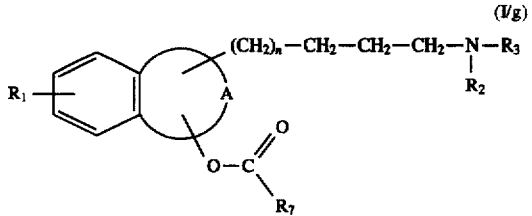

in which n, A, $R_1$, $R_2$, $R_3$ and $R_7$ are as defined above, I10 which may be subjected to a saponification in the presence of sodium hydroxide to obtain a corresponding compound of formula (I/i):

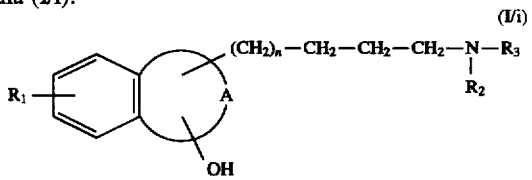

in which n, A, $R_1$, $R_2$ and $R_3$ are as defined above, or subjected to a reduction to obtain a compound of formula (I/j):

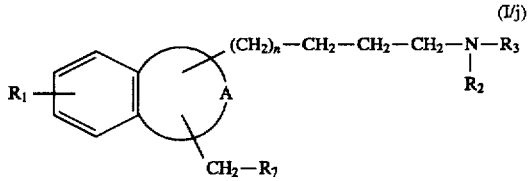

in which n, A, R₁, R₂, R₃ and R₇ are as defined above, it being possible, if so desired, for the compounds of formulae (I/f), (I/g), (I/h), (I/i) and (I/j)

to be purified according to one or more purification methods chosen from crystallization, chromatography on silica gel, extraction, filtration and passage over charcoal or through resin, to be separated, where appropriate, in pure form or in the form of a mixture, into their possible enantiomers or diastereoisomers, or to be salified with a pharmaceutically acceptable base.

The starting materials used in the processes described above are either commercial or are readily accessible to a person skilled in the art from the literature and the examples of preparations given below.

Thus, the compounds of formula (II) are readily accessible to a person skilled in the art by reacting a carboxylic acid of formula (II/a):

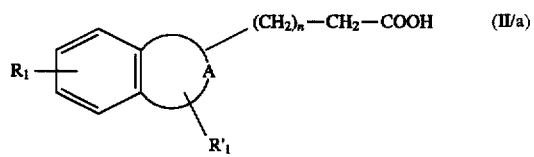

in which n, A, R₁ and R'₁ are as defined in the formula (1), 1) either with methanol in presence of thionyl chloride to yield a compound of formula (II/b):

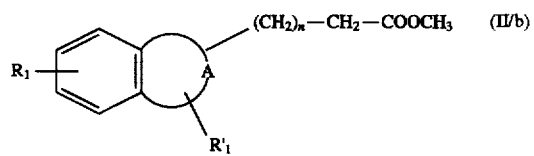

in which n, A, R₁ and R'₁ are as defined above, which is reduced to a compound of formula (II/c):

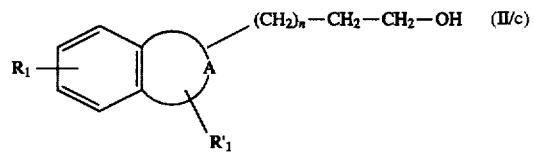

in which n, A, R₁ and R'₁ are as defined above, which, when reacted with methanesulfonyl chloride, yields a compound of formula (II/d)

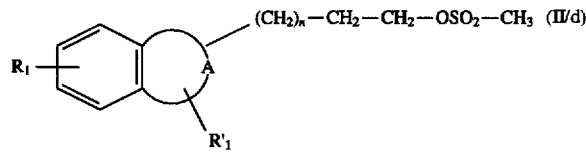

in which n, A, R'₁ and R₁ are as defined above, 2) or with dimethylamine to yield a compound of formula (III/e):

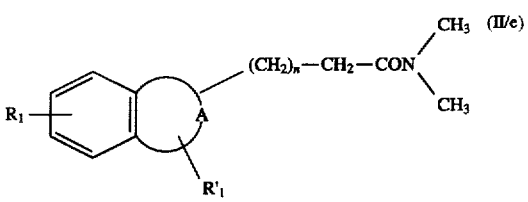

in which n, A, R₁ and R'₁ are as defined above, which is then reduced to a compound of formula (II/g):

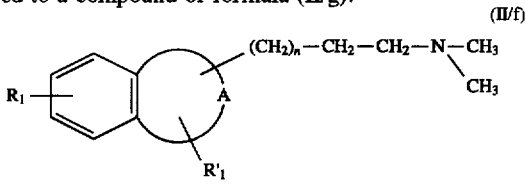

in which n, A, R₁ and R'₁ are as defined above, which is subjected to the action of methyl iodide to yield a compound of formula (II/g):

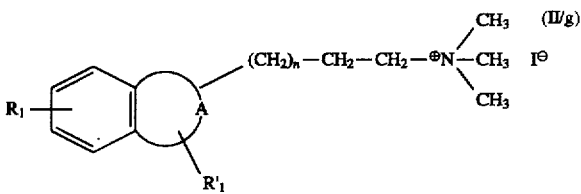

in which n, A, R₁ and R'₁ are as defined above, either of which compounds of formulae (II/d) and (II/g) is reacted with potassium cyanide to give compounds of formula (II/h):

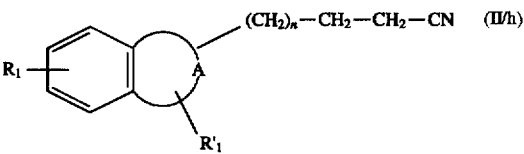

in which n, A, R₁ and R'₁ are as defined above, which is then hydrogenated to yield a compound of formula (II/i):

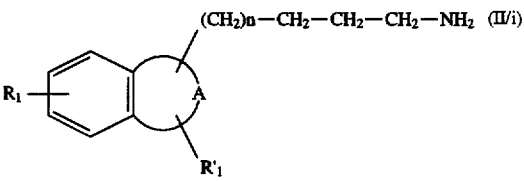

in which n, A, R₁ and R'₁ are as defined above, which is lastly alkylated, where appropriate, to a compound of formula (II/j):

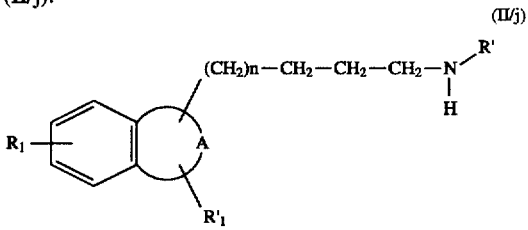

in which n, A, R₁ and R'₁ are as defined above and R' is an alkyl group, the compounds of formula (II/i) and (II/j) collectively forming the compounds of formula (II):

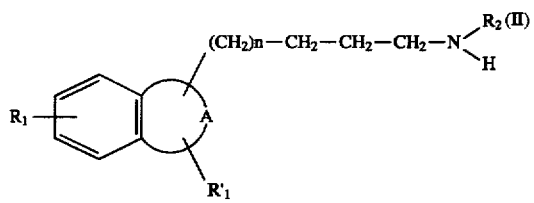

in which n, A, R$_1$, R'$_1$ and R$_2$ are as defined in the formula (I), which may be separated into their enantiomers or diastereoisomers and salified with a pharmaceutically acceptable acid.

For example, the compounds of formula (II) in which n is equal to zero are readily accessible to a person skilled in the art via the preparation process described above.

It is also possible to prepare the compounds of formula (II/k):

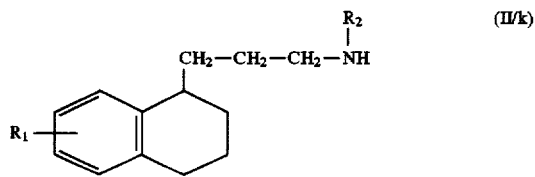

in which R, and R$_2$ are as defined in the formula (i), by reacting a compound of formula (VI):

in which R$_1$ is as defined above, with succinic anhydride to obtain a compound of formula (VII):

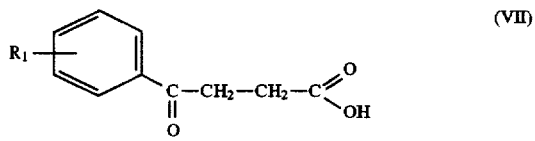

in which R$_1$ is as defined above, which is reduced to obtain a compound of formula (VII):

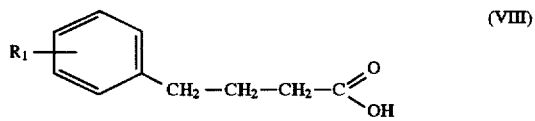

in which R$_1$ is as defined above, which is then cyclized to obtain a compound of formula (IX):

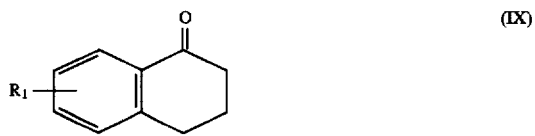

in which R$_1$ is as defined above, which is reacted with diethyl cyanoethylphosphonate to obtain the compound of formula (X):

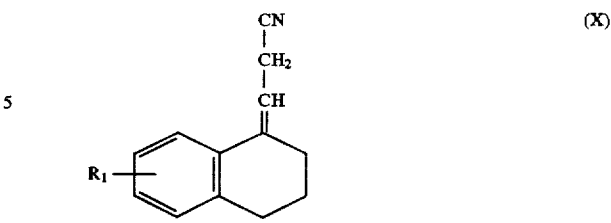

in which R$_1$ is as defined above, which is then hydrogenated to obtain the compound of formula (II/l):

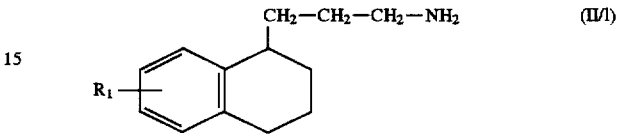

in which R$_1$ is as defined above, which compound of formula (II/l) is alkylated, where appropriate, on the amine function to obtain a compound of formula (II/m):

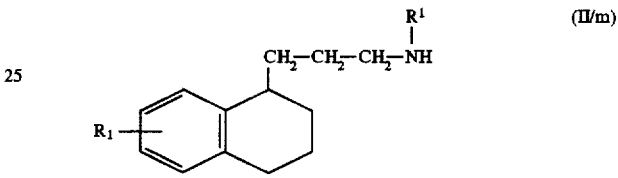

in which R$_1$ is as defined above and R' represents an alkyl group, the compounds of formulae (II/l) and (II/m) collectively forming the compounds of formula (II/j).

Aromatization of the compounds possessing a tetrahydronaphthalene structure as are described above enables the compounds to be obtained which are useful for the preparation of the compounds of formula (I) in which A, with the benzene ring to which it is linked, forms a naphthalene group.

Conversely, reduction of the compounds of formula (I/c) possessing a naphthalene structure enables the compounds of formula (I) to be obtained in which A, with the benzene ring to which it is linked, forms a dihydronaphthalene or tetrahydronaphthalene group, or the compounds which are useful for their preparation.

The intermediate compounds of formula (II/f):

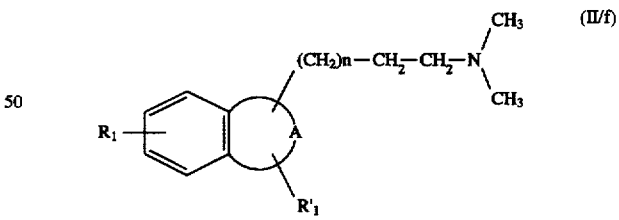

in which A, n, R$_1$ and R'$_1$ are as defined in the formula (1), may also be prepared by the action of formaldehyde on amines of formula (II/n):

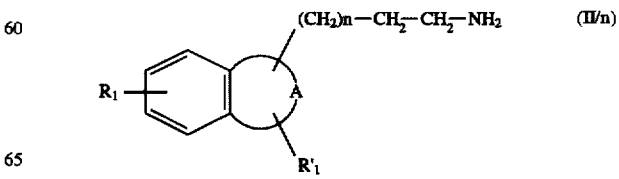

in which A, n, R$_1$ and R'$_1$ are as defined above.

The compounds of formula (I) possess very advantageous pharmacological properties for the clinician.

The compounds of the invention and pharmaceutical compositions containing them prove very useful for the treatment of disorders of the melatoninergic system and of disorders associated with the melatoninergic system.

A pharmacological study of the compounds of the invention showed, in effect, that they were not toxic, were endowed with a very high selective affinity for melatonin receptors and possessed considerable activity with respect to the central nervous system, and particular note was taken of therapeutic properties with respect to sleep disorders, anxiolytic, antipsychotic and analgesic properties and also those affecting the microcirculation which enabled it to be established that the products of the invention are useful in the treatment of stress, sleep disorders, anxiety, seasonal depression, cardiovascular pathologies, insomnia and fatigue due to jet lag, schizophrenia, panic attacks, melancholia, appetite disorders, obesity, psoriasis, insomnia, psychotic disorders, epilepsy, Parkinson's disease, senile dementia, various disorders associated with normal or pathological aging, migraine, memory loss, Alzheimer's disease and also disorders of the cerebral circulation. In another sphere of activity, it is apparent that the products of the invention possess ovulation-inhibiting and immunomodulatory properties and that they are capable of being used in cancer treatment.

The compounds will preferably be used in treatments of seasonal depression, sleep disorders, cardiovascular pathologies, insomnia and fatigue due to jet lag, appetite disorders and obesity.

For example, the compounds will be used in the treatment of seasonal depression and sleep disorders.

The subject of the present invention is also pharmaceutical compositions containing the products of formula (I) in combination with one or more pharmaceutically acceptable excipients.

Among the pharmaceutical compositions according to the invention, there may be mentioned, more especially, those which are suitable for oral, parenteral, nasal, per- or transcutaneous, rectal, perlingual, ocular or respiratory administration, and in particular simple or sugar-coated tablets, sublingual tablets, sachets, packets, hard gelatin capsules, infraglossal preparations, troches, suppositories, creams, ointments, skin gels and ampoules for administration orally or by injection.

The dosage varies according to the patient's sex, age and weight, the administration route and the nature of the therapeutic indication or of any associated treatments, and ranges between 0.1 mg and 1 g per 24 hours taken in 1 or 2 doses, and more especially between 1 and 100 mg, for example between 1 and 10 mg.

The examples which follow illustrate the invention but in no way limit it.

PREPARATION 1: 3-(7-METHOXY-1-NAPHTHYL)PROPYLAMINE HYDROCHLORIDE

METHOD 1:
STAGE A: (7-METHOXY-1- NAPHTHYL)-N,N-DIMETHYLACETAMIDE

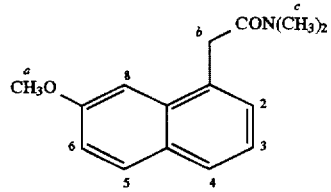

Reactants:
(7-Methoxy-1-naphthyl)acetic acid: 0.032 mol (7 g)
Thionyl chloride: 0.128 mol (9.5 $Gm^3$)
Dimethylamine (25% aqueous solution): 0.390 mol (70 $cm^3$)
Chloroform: 300 $cm^3$
Anhydrous ether: 200 $cm^3$
5% aqueous sodium hydroxide solution: 20 $cm^3$
Procedure:

In a 750-$cm^3$ round-bottomed flask, 7 g of (7-methoxy-1-naphthyl)acetic acid are dissolved in 150 $cm^3$ of chloroform. The mixture is brought to reflux and 9.5 $cm^3$ of thionyl chloride diluted in 150 $cm^3$ of chloroform are then added slowly. The mixture is left refluxing for 2 hours. It is allowed to cool and the solvent is evaporated off under vacuum. The oily residue is dissolved in anhydrous ether. The round-bottomed flask is placed in an ice bath at $-5°$ C., and 70 $cm^3$ of dimethylamine in 25% aqueous solution are added slowly. The mixture is left under stirring for 1 hour. The precipitate obtained is filtrated and then recristallized in the appropriate solvant.
Characteristics:
Molar mass: 243.31 g/mol for $C_{15}H_{17}NO_2$
Melting point: 86°–88° C.
Recrystallization solvent: hexane
Yield: 31%
Elution solvent: ethyl acetate
Rf: 0.32
Appearance: white crystals
Elemental analysis:

|  | C % | H % | N % |
| --- | --- | --- | --- |
| Calculated | 74.04 | 7.04 | 5.76 |
| Found | 74.14 | 7.24 | 5.84 |

Infrared spectroscopic analysis:
3000–2810 $cm^{-1}$ : vCH (alkyl)
1650–1570 $cm^{-1}$ : vCO (amide)
1260 $cm^{-1}$ : $vOCH_3$
Proton NMR spectroscopic analysis ($CDCl_3$, δ, 80 MHz):
3.00 ppm (singlet, 6H): $H_c$
3.95 ppm (singlet, 3 H): $H_a$
4.1 0 ppm (singlet, 2H): $H_b$
7.10–7.40 ppm (unresolved complex, 4H): $H_{2,3,6,8}$
7.60–7.90 ppm (unresolved complex, 2H): $H_{4,5}$

STAGE B: N-[2-(7-METHOXY-1-NAPHTHYL)ETHYL]-N,N-DIMETHYLAMINE HYDROCHLORIDE

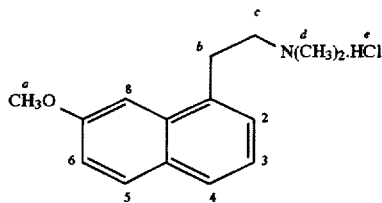

1) From (7-methoxy-1-naphthyl)-N,N-dimethylacetamide

Reactants:
(7-Methoxy-1-naphthyl)-N,N-dimethylacetamide: 0.004 mol (1 g)
Lithium aluminum hydride: 0.053 mol (2 g)
Anhydrous ether: 150 cm$^3$ Procedure:
In a 100-cm$^3$ flask, 1 g of (7-methoxy-1-naphthyl)-N,N-dimethylacetamide is dissolved in ether. Lithium aluminum hydride is added. The mixture is brought to reflux for 3 hours. The amount of 10% aqueous sodium hydroxide solution needed to hydrolyze the excess unreacted hydride is added dropwise. The reaction medium is filtered. The ether phase is extracted with twice 20 cm$^3$ of sodium hydroxide solution, washed with water, dried over sodium sulfate and evaporated under reduced pressure. The residue is dissolved ;in anhydrous ether, anhydrous ether saturated with HCl is added to it and the precipitate is filtered off and recrystallized. Yield: 83%

2) From 2-(7-methoxy-1-naphthyl)ethylamine hydrochloride

Reactants:
2-(7-Methoxy-1-naphthyl)ethylamine hydrochloride: 0.042 mol (10 g)
30% formaldehyde: 0.084 mol (8.5 cm$^3$)
Raney nickel: 2 g
Anhydrous methanol: 200 cm$^3$
Sodium carbonate: 0.042 mol (4.46 g)

Procedure:
In a 250-cm$^3$ flask, 10 g of 2-(7-methoxy-1-naphthyl)ethylamine hydrochloride are dissolved in 100 cm$^3$ of water, and 4.46 g of sodium carbonate are then added gradually. The aqueous phase is extracted with 4 times 50 cm$^3$ of chloroform, the organic phases are washed and are dried over magnesium sulfate and the solvent is evaporated off. The residue is taken up in 200 cm$^3$ of anhydrous methanol, and 2 g of Raney nickel and 8.5 cm$^3$ of 30% formaldehyde are added. The autoclave is placed under a hydrogen pressure of 50 bar for 24 hours. The reaction medium is filtered. The solvent is evaporated off. The residue is taken up with ethyl acetate, and this organic phase is washed with water, dried over magnesium sulfate and then evaporated. The oily residue is dissolved in ether, and anhydrous ether saturated with HCl is added. The precipitate obtained is drained and recrystallized. Yield: 24%

Characteristics:
Molar mass: 265.78 g/mol for $C_{15}H_{20}NOCl$
Melting point: 142°–144° C.
Recrystallization solvent: acetone
Elution solvent: acetone/toluene/cyclohexane (4:4:2) +1 cm$^3$ of triethylamine
Rf: 0.41

Infrared spectroscopic analysis:
3020–2820 cm$^{-1}$: νCH (alkyl)
2700–2300 cm$^{-1}$: νNH+(tertiary amine salt)
1610 and 1590 cm$^{-1}$: νC=C (aromatic)
1250 cm$^{-1}$: νOCH$_3$ Proton NMR spectroscopic analysis (CDCl$_3$, δ, 80 MHz):
2.00 ppm (singlet, 1H): H$_e$, exchangeable in D$_2$O
2.90 ppm (doublet, 6H): H$_d$,J=4.70 Hz
3.30 ppm (multiplet, 2H): H$_b$
3.65 ppm (multiplet, 2H): H$_c$
4.05 ppm (singlet, 3H): H$_a$
7.05–7.40 ppm (unresolved complex, 4H): H$_{2,3,6,8}$
7.40–7.80 ppm (unresolved complex, 2H): H4,5

STAGE C: N,N,N-TRIMETHYL-N-[2-(7-METHOXY-1-NAPHTHYL)ETHYL]-AMMONIUM IODIDE

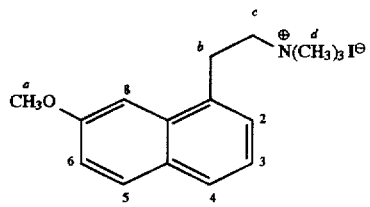

Reactants:
N-[2-(7-Methoxy-1-naphthyl)ethyl]-N,N-dimethylamine hydrochloride: 0.008 mol (2.13 g)
Methyl iodide: 0.080 mol (11.4 g)
Sodium carbonate: 0.008 mol (0.8 g)
Ethanol: 100 cm$^3$.

Procedure:
2.13 g of N-[2-(7-methoxy-1-naphthyl)ethyl]-N,N-dimethylamine hydrochloride are dissolved in water and 0.8 g of sodium carbonate is added gradually. The aqueous phase is extracted with 3 times 50 cm$^3$ of chloroform, and the organic phase is washed with water, dried over magnesium sulfate and evaporated. The residue is taken up in ethanol (50 cm$^3$), and the amine is added to an ice-cold ethanolic solution containing 11.4 g of methyl iodide. The mixture is left in an ice bath for 24 hours. The precipitate obtained is filtered off and recrystallized.

Characteristics:
Molar mass: 371.26 g/mol for $C_{16}H_{22}NOI$
Melting point: 232°–234° C.
Recrystallization solvent: 950 strength alcohol
Yield: 92%

Infrared spectroscopic analysis:
3020–2800 cm–1: νCH (alkyl)
1610 and 1590 cm$^{-1}$: νC=C (aromatic)
1250 cm$^{-1}$: νOCH$_3$ Proton NRM spectroscopic analysis (DMSO-d$_6$, δ, 80 Mhz):
3.30 ppm (singlet, 9H): H$_d$
3.60 ppm (unresolved complex, 4H): H$_{b,c}$
3.95 (singlet, 3H): H$_a$
7.15–7.60 ppm (unresolved complex, 4H): H$_{2,3,6,8}$
7.70–8.00 ppm (unresolved complex, 2H): H$_{4,5}$

METHOD 2:
STAGE A': METHYL (7-METHOXY-1-NAPHTHYL) ACETATE

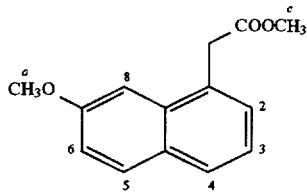

Reactants:
(7-Methoxy-1-naphthyl)acetic acid: 0.023 mol (5 g)
Thionyl chloride: 0.092 mot (6.75 cm$^3$)
Methanol: 150 cm$^3$
Procedure:

In a 250-cm$^3$ flask, 5 g of (7-methoxy-1-naphthyl)acetic acid are dissolved in methanol. The mixture is cooled in an ice bath at −10° C. 6.75 cm3 of thionyl chloride are added dropwise and with stirring using a dropping funnel. The reaction medium is left stirring for 30 minutes. It is evaporated under reduced pressure. The oily residue is dissolved in ethyl acetate, and the organic phase is extracted with 3 times 50 cm$^3$ of 10% potassium carbonate solution and then with water, dried over sodium sulfate and evaporated. The oily residue obtained, which solidifies at room temperature, is recrystallized.

Characteristics:
Molar mass: 230.26 g/mol for $C_{14}H_{14}O_3$
Melting point: 51°–52° C.
Recrystallization solvent: n-hexane
Yield: 94%
Elution solvent: acetone/toluene/cyclohexane (4:4:2)
Rf: 0.73
Elemental analysis:

|  | C % | H % | N % |
|---|---|---|---|
| Calculated | 73.03 | 6.13 | 20.85 |
| Found | 72.86 | 6.18 | 20.75 |

Infrared spectroscopic analysis:
3040–2820 cm$^{-1}$: vCH (alkyl)
1730 cm$^{-1}$: vCO (ester)
1620 and 1600 cm$^{-1}$: vC=C (aromatic)
1260 cm$^{-1}$: vOCH$_3$
Proton NMR spectroscopic analysis (CDCl$_3$, δ, 80 MHz):
3.65 ppm (singlet, 3H): H$_c$
3.90 ppm (singlet, 3H): H$_a$
4.00 ppm (singlet, 2H): H$_b$
7.10–7.45 ppm (unresolved complex, 4H): H$_{2,3,6,8}$
7.60–7.90 ppm (unresolved complex, 2H): H$_{4,5}$

STAGE B': 2-(7-METHOXY-1-NAPHTHYL)ETHANOL

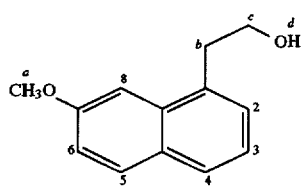

Reactants:
Methyl (7-methoxy-1-naphthyl)acetate: 0.022 mol (5 g)
Lithium aluminum hydride: 60.088 mol (3.34 g)
Anhydrous ether: 100 cm$^3$
Procedure:

3 3.34 g of lithium aluminum hydride are placed in a 250 cm$^3$ flask, and ether is added gently with stirring. Using a dropping funnel, 5 g of methyl (7-methoxy-1-naphthyl) acetate I10 previously dissolved in 50 cm $^3$of ether are added slowly. The reaction medium is left stirring for 30 minutes. It is poured very slowly into a mixture of water and ice so as to hydrolyze the excess unreacted hydride. The reaction medium is filtered. The aqueous phase is extracted with 3 times 50 cm$^3$ of ether, and the ether phases are dried over magnesium sulfate and evaporated. The white solid obtained is recrystallized.

Characteristics:
Molar mass: 202.25 g/mol for $C_{13}H_{14}O_2$
Melting point: 80°–82C.
Recrystallization solvent: cyclohexane
Yield: 82%
Elution solvent: acetone/toluenelcyclohexane (4:4:2)
Rf: 0.34
Appearance: white powder
Elemental analysis:

|  | C % | H % | O % |
|---|---|---|---|
| Calculated | 77.20 | 6.98 | 15.82 |
| Found | 76.91 | 7.13 | 15.71 |

Infrared spectroscopic analysis:
3300–3100 cm$^{-1}$: vOH, broad band
3000–2800 cm$^{-1}$: vCH (alkyl)
1610 and 1590 cm$^{-1}$: vC=C (aromatic)
1250 cm$^{-1}$: vOCH$_3$
1030 cm$^{-1}$: vC—O (alcohol)
Proton NMR spectroscopic analysis (CDCl$_3$, δ, 80 MHz):
1.60 ppm (singlet, 1H): Hd, exchangeable in D$_2$O
3.30 ppm (triplet, 2H): H$_b$ $J_{b-c}$=7.10 Hz
3.90 ppm (singlet, 3H): H$_a$
4.00 ppm (triplet, 2H): H. J$_{c-b}$=7.10 Hz
7.00–7.40 ppm (unresolved complex, 4H): H$_{2,3,6,8}$
10 7.60–7.80 ppm (unresolved complex, 2H): H$_{4,5}$

STAGE C': 2-(7-METHOXY-1-NAPHTHYL)ETHYL MESYLATE

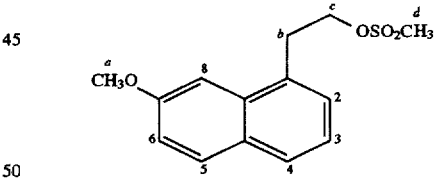

Reactants:
2-(7-Methoxy-1-naphthyl)ethanol: 0.020 mol (4 g)
Mesyl chloride: 0.024 mol (2.75 g)
Triethylamine: 0.024 mol (3.3 cmi)
Dichloromethane: 100 cm3
Procedure:

In a 250-cm$^3$ flask, 4 g of 2-(7-methoxy-1-naphthyl) ethanol are dissolved in 100 cm$^3$ of dichloromethane, and 3.3 cm$^3$ of triethylamine are added. The mixture is cooled in an ice bath at −10° C. and 2.75 g of mesyl chloride are then added dropwise and with stirring. The mixture is left stirring for 30 minutes. The aqueous phase is extracted with 3 times 50 cm$^3$ of dichloromethane, and the organic phase is washed with 3 times 20 cm$^3$ of 1N hydrochloric acid solution and then with water, dried over potassium carbonate and evaporated. The oily residue is recrystallized.

Characteristics:
Molar mass: 280.34 g/mol for $C_{14}H_{16}O_4S$
Melting point: 62°–63° C.
Recrystallization solvent: cyclohexane
Yield: 94%
Elution solvent: acetone/toluene/cyclohexane (4:4:2)
Rf: 0.72
Appearance: white powder
Elemental analysis:

|  | C % | H % | O % |
|---|---|---|---|
| Calculated | 59.98 | 5.76 | 22.83 |
| Found | 59.83 | 5.60 | 22.59 |

Infrared spectroscopic analysis:
3000–2820 cm$^{-1}$: vCH (alkyl)
1620 and 1590 cm$^{-1}$: vC=C (aromatic)
1330 cm$^{-1}$: vSO$_2$ asymmetric
1240 cm$^{-1}$: vOCH$_3$
1150 cm$^{-1}$: vSO$_2$ symmetrical
Proton NMR spectroscopic analysis (CDCl$_3$, δ, 80 MHz):
2.85 ppm (singlet, 3H): H$_d$
3.50 ppm (triplet, 2H): H$_b$ J$_{b-c}$=8.00 Hz
3.95 ppm (singlet, 3H): H$_a$
4.55 ppm (triplet, 2H): H$_c$ J$_{c-b}$=8.00 Hz
7.10–7.40 ppm (unresolved complex, 4H): H$_{2,3,6,8}$
7.60–7.80 ppm (unresolved complex, 2H): H$_{4,5}$

STAGE D: 3-(7-METHOXY-1-NAPHTHYL) PROPIONITRILE

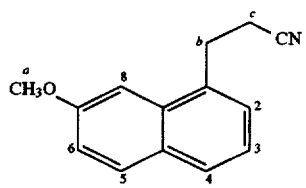

1) From the quaternary ammonium salt
Reactants:
Trimethyl-[2-(7-methoxy-1-naphthyl)ethyl]ammonium iodide: 0.002 mol (0.74 g)
Potassium cyanide: 0.006 mol (0.4 g)
Dimethylformamide: 10 cm$^3$
Procedure:
10 cm$^3$ of dimethylformamide and 0.74 g of quaternary ammonium salt are placed in a 100-cm$^3$ flask. The mixture is heated to 75° C. 0.4 g of potassium cyanide is then added. The medium is left at 75° C. for 2 hours. It is allowed to cool. It is poured into a mixture of water and ice. The precipitate obtained is filtered off and recrystallized. Yield: 10% (crude product)

2) From the mesylate
Reactants:
2-(7-Methoxy-1-naphthyl)ethyl mesylate: 0.015 mol (4.2 g)
Potassium cyanide: 0.045 mol (2.93 g)
Dimethyl sulfoxide: 20 cm$^3$
Procedure:
In a 100-cm$^3$ flask, 4.2 g of 2-(7-methoxy-1-naphthyl)ethyl mesylate are dissolved in 20 cm$^3$ of dimethyl sulfoxide, and 2.93 g of potassium cyanide are added. The medium is refluxed for 2 hours. It is allowed to cool and is poured into a water/ice mixture. The nitrile which has precipitated is filtered off and recrystallized. Yield: 95%
Characteristics:
Molar mass: 211.26 g/mol for $C_{14}H_{13}NO$
Melting point: 62°–64° C.
Recrystallization solvent: hexane
Elution solvent: acetone/toluene/cyclohexane (4:4:2)
Rf: 0.80
Appearance: white powder
Elemental analysis:

|  | C % | H % | O % |
|---|---|---|---|
| Calculated | 79.60 | 6.20 | 7.57 |
| Found | 79.67 | 6.20 | 7.72 |

Infrared spectroscopic analysis:
3020–2820 cm$^{-1}$: vCH (alkyl)
2220 cm$^{-1}$: vCN (nitrile)
1610 and 1590 cm$^{-1}$: vC=C (aromatic)
1240 cm$^{-1}$: vOCH$_3$
Proton NMR spectroscopic analysis (CDCl$_3$, δ, 80 MHz):
2.80 ppm (triplet, 2H): H$_c$ J$_{b-c}$=7.70 Hz 3.40 ppm (triplet, 2H): H$_b$ J$_{b-c}$=7.70 Hz 4.00 ppm (singlet, 3H): H$_a$
7.20–7.40 ppm (unresolved complex, 4H): H$_{2,3,6,8}$
7.70–7.90 ppm (unresolved complex, 2H): H$_{4,5}$

STAGE E: 3-(7-METHOXY-1-NAPHTHYL) PROPYLAMINE HYDROCHLORIDE

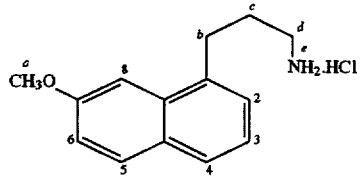

Reactants:
3-(7-Methoxy-1-naphthyl)propionitrile: 0.006 mol (1.51 g)
Raney nickel: 1 g
Ethanol: 150 cm$^3$
Procedure:
1.51 g of 3-(7-methoxy-1-naphthyl)propionitrile previously dissolved in 150 cm$^3$ of ethanol are poured into an autoclave, and 1 g of Raney nickel is added. The solution is saturated with ammonia. It is placed under a hydrogen pressure (50 bars) and at 60° C. It is left stirring for 12 hours. It is allowed to cool to room temperature. The medium is filtered and the solvent is evaporated off. The residue is redissolved in anhydrous ether, and anhydrous ether saturated with HCl is added. The hydrochloride obtained is drained and then recrystallized.
Characteristics:
Molar mass: 251.75 g/mol for $C_{14}H_{18}NOCl$
Melting point: 197°–200° C.
Recrystallization solvent: cyclohexane/ethanol (1:1)
Yield: 91%
Elution solvent: acetone/toluene/cyclohexane (4:4:2)
Rf: 0.05
Appearance: white solid
Elemental analysis:

|  | C % | H % | O % | N % |
|---|---|---|---|---|
| Calculated | 66.79 | 7.21 | 6.36 | 5.56 |
| Found | 66.79 | 7.22 | 6.35 | 5.62 |

Infrared spectroscopic analysis:
3100–2640 cm$^{-1}$: vNH$_3$+, broad peak
1620 and 1590 cm$^{-1}$: vC=C (aromatic)

1250 cm$^{-1}$: vOCH$_3$

Proton NMR spectroscopic analysis (DMSO-d$_6$, δ, 300 MHz)

2.00 ppm (multiplet, 2H): H$_c$
2.90 ppm (triplet, 2H): H$_b$ J$_{b-c}$ =7.72 Hz
3.10 ppm (triplet, 2H): H$_d$ J$_{d-c}$=7.27 Hz
3.95 ppm (singlet, 3H): H$_a$
7.15–7.40 ppm (unresolved complex, 4H): H$_{2,3,6,8}$
7.74 ppm (doublet, 1 H): H$_4$ $_{|Jortho}$=7.78 Hz
7.85 ppm (doublet, 1 H): H$_5$ J$_{ortho}$=8.94 Hz
8.12 ppm (singlet, 3H): NH$_3^+$, exchangeable in D$_2$O

PREPARATION 2: 3-(7-ETHYL-1,2,3,4-TETRAHYDRO-1-NAPHTHYL)PROPYLAMINE

STAGE A: 4-OXO-4-(4-ETHYLPHENYL)BUTYRIC ACID

Reactants:
Ethylbenzene: 0.05 mol (5 cm$^3$)
Aluminum chloride: 0.02 mol (2.6 g)
Succinic anhydride: 0.01 mol (1 g)
Procedure:

5 cm$^3$ of ethylbenzene and 2.6 g of aluminum chloride are mixed with magnetic stirring in a 50-cm$^3$ flask. The solution is cooled in an ice bath and 1 g of succinic anhydride is then added. The reaction mixture is stirred for 1 h 30 min at a temperature of 0° C. and then for 3 h at room temperature. It is poured into ice. The resulting mixture is acidified by adding 1N hydrochloric acid (pH 3–4). It is extracted with 3 volumes of ether. The organic phases are washed 3 times with 10% potassium carbonate solution. The aqueous phases are combined and acidified by adding concentrated hydrochloric acid. The precipitate obtained is drained and then recrystallized.

Characteristics:
Molar mass: 206.23 g/mol for C$_{12}$H$_{14}$O$_3$
Appearance: white powder
Recrystallization solvent: cyclohexane
Yield: 57%
Melting point: 106°–108° C.
Rf: 0.36
Eluent: acetone/toluene/cyclohexane (2:2:1)
Infrared spectroscopic analysis:
2960–2920 cm: valkyl CH
1710 cm$^{-1}$: vketone CO
1670 cm$^{-1}$: vacid CO
1600 cm$^{-1}$: varomatic C=C
Proton NMR spectroscopic analysis (80 MHz, DMSO-d$_6$, δ):

1.2 ppm (triplet, 3H): CH$_3$ (a) J$_{a-b}$=6.60 Hz
2.6 ppm (multiplet, 4H): CH$_2$ (b) and CH$_2$ (d) J$_{b-a}$=J$_{d-c}$=6.60 Hz
3.2 ppm (triplet, 2H): CH$_2$ (c) J$_c$=6.60 Hz
7.4 ppm (doublet, 2H): H$_3$ and H$_5$ J$_{ortho}$=8.80 Hz
7.9 ppm (doublet, 2H): H$_2$ and H$_6$ J$_{ortho}$=8.80 Hz
12.1 ppm (multiplet, 1H): COOH
Mass spectrometric analysis:
m/e 206: M$^+$
m/e 207: (M+1)$^+$

STAGE B: 4-(4-ETHYLPHENYL)BUTYRIC ACID

Reactants:
4-Oxo-4-(4-ethylphenyl)butyric acid (stage A): 0.012 mol (2.5 g)
Triethylsilane: 0.028 mol (3.2 g)
Trifluoroacetic acid: 0.12 mol (19 cm$^3$)
Procedure:

In a 100-cm$^3$ flask, 2.5 g of 4-oxo-4-(4-ethylphenyl)butyric acid are dissolved with magnetic stirring in 19 cm$^3$ of trifluoroacetic acid. 3.2 g of triethylsilane are added dropwise.

The reaction mixture is stirred for 86 hours at room temperature. It is poured into ice. It is extracted with 3 volumes of ether. The organic phases are washed 3 times with 10% potassium carbonate solution. The aqueous phases are combined and then acidified by adding concentrated hydrochloric acid until the pH is 3–4. The precipitate obtained is drained and then recrystallized.

Characteristics:
Molar mass: 192.25 g/mol for C$_{12}$H$_{16}$O$_2$
Appearance: white powder
Recrystallization solvent: water
Yield: 65%
Melting point: 71°–73° C.
Rf: 0.67
Eluent: acetone/toluene/cyclohexane (2:2:1)
Infrared spectroscopic analysis:
3280–2780 cm$^{-1}$: vacid OH
2940–2850 cm$^{-1}$: valkyl CH
1680 cm$^{-1}$: vacid CO
1510 cm$^{-1}$: varomatic C=C
Proton NMR spectroscopic analysis (300 MHz, DMSO-d$_6$, δ):

1.14 ppm (triplet, 3H): CH$_3$ (a) J$_{a-b}$=7.63 Hz
1.76 ppm (multiplet, 2H): CH$_2$ (d)
2.20 ppm (triplet, 2H): CH$_2$ (e) J$_{d-e}$=7.65 Hz
2.55 ppm (multiplet, 4H): CH$_2$ (c) and CH$_2$ (b)
7.11 ppm (multiplet, 6H): aromatic H
Acid OH not observed
Mass spectrometric analysis:
m/e 192: M$^+$
m/e 193: (M+1)$^+$

STAGE C: 7-ETHYLTETRALONE

Reactants:
4-(4-Ethylphenyl)butyric acid (stage B): 0.013 mol (2.5 g)
Polyphosphoric acid: 25 g
Procedure:

25 g of polyphosphoric acid are poured into a 100-cm$^3$ ground-necked round-bottomed flask. 2.5 g of 4-(4-ethylphenyl)butyric acid are added. The reaction mixture is stirred for 6 h at a temperature of 45° C. It is poured into ice. The resulting mixture is extracted with 3 volumes of ether. The organic phases are washed 3 times with 10% potassium carbonate solution, dried over magnesium sulfate and then evaporated to dryness.

The oil obtained is purifed by column chromatography.
Characteristics:
Molar mass: 174.23 g/mol for $C_{12}H_{14}O_2$
Appearance: colorless oil
Rf: 0.35
Eluent: toluene/cyclohexane (1:2)
Yield: 55%
Infrared spectroscopic analysis:
3010 cm$^{-1}$: varomatic CH
2980–2860 cm$^{-1}$: valkyl CH
1680 cm$^{-1}$: vketone CO
1605 cm$^{-1}$: varomatic C=C
Proton NMR spectroscopic analysis (300 MHz, DMSO-d$_6$, δ:
1.13 ppm (triplet, 3H): CH$_3$ (a), $J_{a-b}$=7.68 Hz
2.01 ppm (multiplet, 2H): CH$_2$ (3)
2.59 ppm (multiplet, 4H): CH$_2$ (b) and CH$_2$ (4)
2.88 ppm (triplet, 2H): CH$_2$ (2), $J_{2-3}$=5.77 Hz
7.25 ppm (doublet, 1H): H$_5$, $J_{ortho}$=8.59 Hz
7.39 ppm (doublet of doublet, 1H): H$_6$, $J_{ortho}$=8.59 Hz, $J_{meta}$=2.14 Hz
7.70 ppm (doublet, 1H): H$_8$, $J_{meta}$=2.14 Hz
Mass spectrometric analysis:
m/e 174 M$^+$
m/e 175 (M +1)$^+$

STAGE D: 3-(7-ETHYL-1,2,3,4-TETRAHYDRO-1-NAPHTHYL)PROPYLAMINE

The compound obtained in the preceding stage is then reacted with a cyano reagent so as to obtain 3-(7-ethyl-1,2,3,4-tetrahydro-1-naphthyl)propionitrile, which is then hydrogenated using a procedure similar to that in stage D of Preparation 1 to obtain the compound of the title.

PREPARATION 3: 3-(5-ETHYLBENZO[b]THIOPHEN-3-YL)PROPYLAMINE

PREPARATION 4: 3-(7-METHYL-1,2,3,4-TETRAHYDRO-1-NAPHTHYL)PROPYLAMINE

Using the procedure described in Preparation 2, but starting from toluene instead of from ethylbenzene, the compound of the title is obtained.

PREPARATION 5: 3-(7-PROPYL-1,2,3,4-TETRAHYDRO-1-NAPHTHYL)PROPYLAMINE

Using the procedure described in Preparation 2, but replacing ethylbenzene by propylbenzene, the compound of the title is obtained.

PREPARATION 6: 3-(7-BUTYL-1,2,3,4-TETRAHYDRO-1-NAPHTHYL)PROPYLAMINE

Using the procedure described in Preparation 2, but replacing ethylbenzene by butylbenzene, the compound of the title is obtained.

PREPARATION 7: 3-(5-METHYLBENZOFURAN-3-YL)PROPYLAMINE

PREPARATION 8: 3-(5-ETHYLBENZOFURAN-3-YL)PROPYLAMINE

PREPARATION 9: 3-(7-METHOXY-1,2,3,4-TETRAHYDRO-1-NAPHTHYL)PROPYLAMINE

PREPARATION 10: 3-(5-METHOXYBENZOFURAN-3-YL)PROPYLAMINE

PREPARATION 11: 3-(1-NAPHTHYL)PROPYLAMINE

PREPARATION 12: 3-(5-METHOXYBENZOTHIOPHEN-3-YL)PROPYLAMINE

PREPARATION 13: 3-(5-METHOXY-3-INDOLYL)PROPYLAMINE

Pol. J. Pharmacol. Pharm. 1979, 31(2), pp. 149–156

PREPARATION 14: 3-(5-METHYLBENZOTHIOPHEN-3-YL)PROPYLAMINE

Monatsch. Chem. 1968, 99(5), pp. 2095–9

PREPARATION 15: 4-(7-METHOXY-1-NAPHTHYL)BUTYLAMINE

Stage A: 3-(7-Methoxy-1-naphthyl)propanoic acid

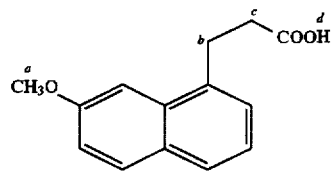

Reactants:
3-(7-Methoxy-1-naphthyl)propionitrile: 1 g (4.7×10$^{-3}$ mol)
6N aqueous sodium hydroxide solution: 10 cm$_3$ (6×10$^{-2}$ mol)
Methanol: 10 cm$^3$ Procedure:
The 3-(7-methoxy-1-naphthyl)propionitrile is dissolved in 10 cm$^3$ of methanol in a 100-cm$^3$ flask. The aqueous sodium hydroxide solution is added and the medium is brought to reflux overnight. The medium is allowed to cool and is acidified with 6N aqueous HCl solution, and the precipitate formed is then filtered off. It is recrystallized.
Characteristics:
Molar mass: 230.26 g for $C_{14}H_{14}O_3$
Appearance: white solid
Melting point: 154°–155° C.
Rf: 0.40
Eluent: acetone/toluene/cyclohexane (hereinafter ATC) (4:4:2)
Yield: 90%
Recrystallization solvent toluene
Elemental analysis:

|  | C % | H % | O % |
|---|---|---|---|
| Calculated | 73.03 | 6.13 | 20.85 |
| Found | 73.14 | 6.20 | 20.65 |

Infrared spectroscopic analysis:
1700 cm$^{-1}$: vacid CO
1620 and 1600 cm$^{-1}$: vC=C
1260 cm$^{-1}$: vCH$_3$O
NMR spectroscopic analysis (80 MHz, DMSO, δ):
2.65 ppm (triplet, 2H): H$_b$ $J_{b-c}$=7.60 Hz
3.30 ppm (triplet, 2H): H$_c$ $J_{c-b}$=7.60 Hz
3.90 ppm (singlet, 3H): H$_a$
7.10–7.40 ppm (unresolved complex, 4H): H$_{2,3,6,8}$
7.60–7.95 ppm (unresolved complex, 2H): H$_{4,5}$
12.20 ppm (signal, 1H): H$_d$ exchangeable in D$_2$O
STAGE B: METHYL 3-(7-METHOXY-1-NAPHTHYL)PROPANOATE

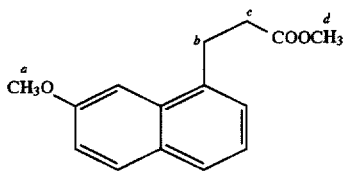

Reactants:
3-(7-Methoxy-1-naphthyl)propanoic acid: 0.2 g (0.9×10⁻³ mol)
Thionyl chloride: 0.25 cm³ (3.5×10⁻³ mol)
Methanol: 20 cm³
Procedure:
In a 100-cm³ flask placed in an ice bath at −50° C., the acid is dissolved in the methanol. The thionyl chloride is added dropwise and the mixture is left stirring for 1 h. It is evaporated, and the residue is taken up with 10 cm³ of ether. The organic phase is washed with 10% aqueous potassium carbonate solution and with water. It is dried over $CaCl_2$, filtered and concentrated in a rotary evaporator.
Characteristics:
Molar mass: 244.29 g for $C_{15}H_{16}O_3$
Appearance: oil
Rf: 0.67
Eluent: ATC (4:4:2)
Yield: 89 %
Elemental analysis:

|  | C % | H % | O % |
| --- | --- | --- | --- |
| Calculated | 73.75 | 6.60 | 19.65 |
| Found | 73.41 | 6.63 | 19.47 |

Infrared spectroscopic analysis:
3020–2800 cm⁻¹: νCH
1730 cm⁻¹: νester CO
1620 and 1590 cm⁻¹: νC=C
1250 cm⁻¹: νCH₃O
NMR spectroscopic analysis (300 MHz, CDCl₃, δ):
2.75 ppm (triplet, 2H): $H_b$ $J_{b-c}$=7.95 Hz
3.34 ppm (triplet, 2H): $H_c$ $J_{c-b}$=7.94 Hz
3.68 ppm (singlet, 3H): $H_d$
20 3.90 ppm (singlet, 3H): $H_a$
7.13–7.30 ppm (unresolved complex, 4H): $H_{2,3,6,8}$
7.63 ppm (doublet, 1H): $H_4$ $J_{ortho}$=7.77 Hz
7.73 ppm (doublet, 1H): $H_5$ $J_{ortho}$=8.95 Hz
STAGE C: 3-(7-METHOXY-1-NAPHTHYL)PROPANOL

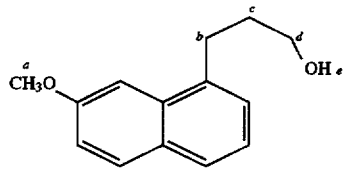

Reactants:
Methyl 3-(7-methoxy-1-naphthyl)propanoate: 0.5 g (2×10⁻³ mol)
LiAlH₄: 0.3 g (8×10⁻³ mol)
Anhydrous ether: 10 cm³
Procedure:
LiAlH₄ and the ether are introduced into a 50-cm³ flask placed in an ice bath at −5° C., and the ester previously diluted in ether is then added dropwise. The medium is left stirring for 1 h and is hydrolyzed by pouring it into ice-cold water. The medium is filtered and extracted with ether. The organic phase is dried, filtered and evaporated.
Characteristics:
Molar mass: 217.29 g $C_{14}H_{16}O_2$
Appearance: white solid
Melting point: 38°–39° C.
Rf: 0.13
Eluent: chloroform
Yield: 88%
Recrystallization solvent: cyclohexane
Elemental analysis:

|  | C % | H % | O % |
| --- | --- | --- | --- |
| Calculated | 77.39 | 7.42 | 14.73 |
| Found | 77.35 | 7.49 | 14.68 |

Infrared spectroscopic analysis:
3300 cm⁻¹: νOH broad band
3040–2800 cm⁻¹: νCH
1620 and 1590 cm⁻¹: νC=C
1250 cm⁻¹: νCH₃O
NMR spectroscopic analysis (300 MHz, CDCl₃, δ):
2.00–2.10 ppm (multiplet, 2H): $H_c$
25 3.15 ppm (triplet, 2H): $H_b$ $J_{b-c}$=7.59 Hz
3.75 ppm (triplet, 2H): $H_d$ $J_{d-c}$=6.24 Hz
3.95 ppm (singlet, 3H): $H_a$
7.13–7.37 ppm (unresolved complex, 4H): $H_{2,3,6,8}$
7.66 ppm (doublet, 1H): $H_4$ $J_{ortho}$=7.83 Hz
7.76 ppm (doublet, 1H): $H_5$ $J_{ortho}$=8.92 Hz
STAGE D: 3-(7-METHOXY-1-NAPHTHYL)PROPYL MESYLATE

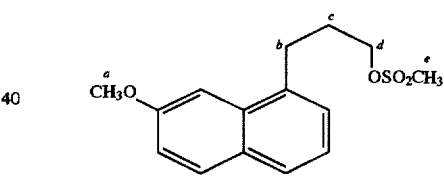

Reactants:
3-(7-Methoxy-1-naphthyl)propanol: 5.1 g (23.5×10⁻³ mol)
CH₃SO₂Cl: 3.3 g (28.2×10⁻³ mol)
NEt₃: 3.9 cm³ (28.2×10⁻³ mol)
CH₂Cl₂: 100 cm³
Procedure:
In a 250-cm³ round-bottomed flask, the 3-(7-methoxy-1-naphthyl)propanol is dissolved in CH₂Cl₂. The triethylamine is added. The round-bottomed flask is placed in an ice and salt bath (−50° C.). The mesyl chloride is added dropwise. The mixture is left stirring for 2 h. The organic phase is washed with 3×20 cm³ HCl and then with water until the aqueous washings are neutral. The organic phase is dried over CaCl₂, filtered and concentrated in a rotary evaporator. The solid obtained is recrystallized.
Characteristics:
Molar mass: 294.37 g for $C_{15}H_{18}O_4S$
Melting point: 52°–54° C.
Eluent: chloroform-methanol (9-1)
Rf: 0.71
Yield: 71%
Recrystallization solvent: toluene/cyclohexane (1:3)

Elemental analysis:

|  | C % | H % | O % |
|---|---|---|---|
| Calculated | 61.20 | 6.16 | 21.74 |
| Found | 61.29 | 6.12 | 21.68 |

Infrared spectroscopic analysis:
3040–2820 cm$^{-1}$: valkyl CH
1610 and 1590 cm$^{-1}$: vC=C
1330 cm$^{-1}$: vSO$_2$ asymm.
1260 cm$^{-1}$: vOCH$_3$
1170 cm$^{-1}$: vSO$_2$ symm.
NMR spectroscopic analysis (300 MHz, DMSO, δ):
2.08 ppm (multiplet, 2H): H$_c$
3.12 ppm (triplet, 2H): H$_b$ J$_{b-c}$=7.75 Hz
3.22 ppm (singlet, 3H): H$_e$
3.92 ppm (singlet, 3H): H$_a$
4.32 ppm (triplet, 2H): H$_d$ J$_{d-c}$=6.20 Hz
7.19 ppm (doublet of doublet, 1H): H$_6$ J$_{ortho}$=8.93 Hz J$_{meta}$=2.38 Hz
7.26–7.37 ppm (unresolved complex, 3H): H$_{2,3,8}$
7.72 ppm (doublet, 1H): H$_4$ J=7.88 Hz
7.85 ppm (doublet, 1H): H$_5$ J=8.90 Hz

STAGE E: 4-(7-METHOXY-1-NAPHTHYL) BUTYRONITRILE

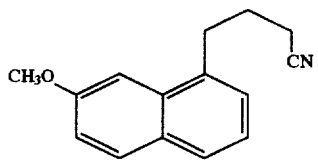

Reactants:
3-(7-Methoxy-1-naphthyl)propyl mesylate: 3 g (10.2×10$^{-3}$ mol)
KCN: 2 g (30.6×10$^{-3}$ mol)
DMSO: 20 cm$^3$
Procedure:
In a 100-cm$^3$ flask, the 3-(7-methoxy-1-naphthyl)propyl mesylate obtained in stage D is dissolved in DMSO. KCN is added and the mixture is brought to reflux for 2 h. It is allowed to cool. It is poured into a water/ice mixture. The resulting mixture is extracted with ether. The organic phase is washed with water, dried over CaCl$_2$ and evaporated. The product obtained is recrystallized.
Characteristics:
Molar mass: 225.29 g for C$_{15}$H$_{15}$NO
Melting point: 52°–54° C.
Rf: 0.39
Eluent: ATC (2:3:5)
Yield: 90%
Recrystallization solvent: alcohol/water (1:5)
Elemental analysis:

|  | C % | H % | O % | N % |
|---|---|---|---|---|
| Calculated | 79.97 | 6.71 | 7.10 | 6.22 |
| Found | 79.58 | 6.78 | 7.49 | 6.15 |

Infrared spectroscopic analysis:
3040–2820 cm$^{-1}$: valkyl CH
2240 cm$^{-1}$: vCN
1620 and 1590 cm$^{-1}$: vC=C
1250 cm$^{-1}$: vOCH$_3$ NMR spectroscopic analysis (300 MHz, CDCl$_3$, δ):
2.09 ppm (multiplet, 2H): H$_c$
2.35 ppm (triplet, 2H): H$_d$ J$_{d-c}$=6.87 Hz
3.18 ppm (triplet, 2H): H$_b$ J$_{b-c}$=7.44 Hz
3.94 ppm (singlet, 3H): H$_a$
7.16 ppm (doublet of doublet, 1H): H$_6$ J$_{ortho}$=8.91 Hz J$_{meta}$=2.44 Hz
7.23–7.30 ppm (unresolved complex, 3H): H$_{2,3,8}$
7.67 ppm (doublet of doublet, 1H): H$_4$ J$_{ortho}$=7.31 Hz J$_{meta}$=1.77 Hz
7.76 ppm (doublet, 1H): H$_5$ J$_{ortho}$=8.91 Hz

STAGE F: 3-(7-METHOXY-1-NAPHTHYL) BUTYLAMINE

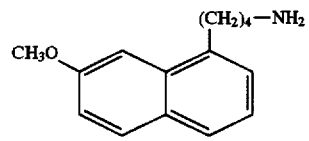

The compound obtained in stage E is hydrogenated in the presence of Raney nickel so as to obtain the product of the title.

PREPARATION 16: N-METHYL-N-[3-(7-METHOXY-1-NAPHTHYL)PROPYL]AMINE HYDROCHLORIDE

N-[3-(7-Methoxy-1-naphthyl)propyl]amine hydrochloride obtained in Preparation 1 is methylated to lead to the formation of N-methyl-N-[3-(7-methoxy-1-naphthyl) propyl]amine hydrochloride.

PREPARATION 17: 3-(7-ETHOXY-1-NAPHTHYL)PROPYLAMINE

Using the procedure described in Preparation 1, but starting from (7-ethoxy-1-naphthyl)acetic acid, the compound of the title is obtained.

PREPARATION 18: 3-(7-PROPOXY-1-NAPHTHYL)PROPYLAMINE

Using the procedure described in Preparation 1, but starting from (7-propoxy-1-naphthyl)acetic acid, the compound of the title is obtained.

PREPARATION 19: 3-(7-BUTYLOXY-1-NAPHTHYL)PROPYLAMINE

Using the procedure described in Preparation 1, but starting from (7-butyloxy-1-naphthyl)acetic acid, the compound of the title is obtained.

PREPARATION 20: 3-(7-PENTOXY-1-NAPHTHYL)PROPYLAMINE

Using the procedure described in Preparation 1, but starting from (7-pentoxy-1-naphthyl)acetic acid, the compound of the title is obtained.

PREPARATION 21: 3-(7-HEXYLOXY-1-NAPHTHYL)PROPYLAMINE

Using the procedure described in Preparation 1, but starting from (7-hexyloxy-1-naphthyl)acetic acid, the compound of the title is obtained.

PREPARATION 22: 3-(7-CYCLOHEXYLOXY-1-NAPHTHYL)PROPYLAMINE

Using the procedure described in Preparation 1, but starting from (7-cyclohexyloxy-1-naphthyl)acetic acid, the compound of the title is obtained.

PREPARATION 23: 3-(7-CYCLOPROPYLMETHOXY-1-NAPHTHYL)PROPYLAMINE

Using the procedure described in Preparation 1, but starting from (7-cyclopropylmethoxy-1-naphthyl)acetic acid, the compound of the title is obtained.

PREPARATION 24: 3-(7-METHYL-1-NAPHTHYL)PROPYLAMINE

Using the procedure described in Preparation 1, but starting from (7-methyl-1-naphthyl)acetic acid, the compound of the title is obtained.

PREPARATION 25: 3-(7-ETHYL-1-NAPHTHYL)PROPYLAMINE

Using the procedure described in Preparation 1, but starting from (7-ethyl-1-naphthyl)acetic acid, the compound of the title is obtained.

PREPARATION 26: 3-(7-PROPYL-1-NAPHTHYL)PROPYLAMINE

Using the procedure described in Preparation 1, but starting from (7-propyl-1-naphthyl)acetic acid, the compound of the title is obtained.

PREPARATION 27: 3-(7-BUTYL-1-NAPHTHYL)PROPYLAMINE

Using the procedure described in Preparation 1, but starting from (7-butyl-1-naphthyl)acetic acid, the compound of the title is obtained.

PREPARATION 28: 3-(7-PENTYL-1-NAPHTHYL)PROPYLAMINE

Using the procedure described in Preparation 1, but starting from (7-pentyl-1-naphthyl)acetic acid, the compound of the title is obtained.

PREPARATION 29: 3-(7-HEXYL-1-NAPHTHYL)PROPYLAMINE

Using the procedure described in Preparation 1, but starting from (7-hexyl-1-naphthyl)acetic acid, the compound of the title is obtained.

PREPARATION 30: 6-(7-METHOXY-1-NAPHTHYL)HEXYLAMINE

EXAMPLE 1: N-[3-(7-METHOXY-1-NAPHTHYL)PROPYL]ACETAMIDE

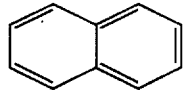

Reactants:
3-(7-Methoxy-1-naphthyl)propylamine hydrochloride: 0.005 mol (1.26 g) (Preparation 1)
Potassium carbonate: 0.015 mol
Acetyl chloride: 0.010 mol
Chloroform: 50 cm$^3$
Procedure:

After 0.005 mol (equivalent to 1.26 g) of 3-(7-methoxy-1-naphthyl)propylamine hydrochloride has been dissolved in 20 cm$^3$ of water, 0.015 mol of potassium carbonate is added. The amine precipitates. Thereafter, 50 cm$^3$ of chloroform are added and 0.010 mol of acetyl chloride is added dropwise. The medium is left stirring for 2 hours. It is acidified with 2N of hydrochloric acid and then stirred for 15 minutes. The aqueous phase is extracted with 3 times 50 cm$^3$ of chloroform. The organic phases are washed with water, dried over calcium chloride and evaporated. Purification of the products is performed either by recrystallization or by column chromatography.

Characteristics:
Molar mass: 257.33 g/mol for $C_{16}H_{19}NO_2$
Melting point: 66°–68° C.
Recrystallization solvent: cyclohexane
Yield: 56%
Elution solvent: acetone/toluene/cyclohexane (4:4:2)
Rf: 0.25
Elemental analysis:

|  | C % | H % | O % | N % |
|---|---|---|---|---|
| Calculated | 74.68 | 7.44 | 12.43 | 5.44 |
| Found | 74.83 | 7.61 | 12.21 | 5.26 |

Infrared spectroscopic analysis:
3300 cm$^{-1}$: νNH (amide)
3020–2800 cm$^{-1}$: νCH (alkyl)
1630 cm$^{-1}$: νCO (amide)
1590 cm$^{-1}$: νC=C (aromatic)
1250 cm$^{-1}$: νOCH$_3$
Proton NMR spectroscopic analysis (DMSO-d$_6$, δ, 300 MHz):
1.70 ppm (multiplet, 2H): H$_c$
1.83 ppm (singlet, 3H): H$_f$
3.00 ppm (triplet, 2H): H$_b$ J$_{b-c}$=7.70 Hz
3.14 ppm (triplet, 2H): H$_d$ J$_{d-c}$=7.27 Hz
3.91 ppm (singlet, 3H): H$_a$
7.14–7.36 ppm (unresolved complex, 4H): H$_{2,3,6,8}$
7.70 ppm (doublet, 1H): H$_4$ J$_{ortho}$=7.83 Hz
7.84 ppm (doublet, 1H): H$_5$ J$_{ortho}$=8.95 Hz
7.96 ppm (signal, 1H): H$_e$

EXAMPLE 2: N-[3-(7-METHOXY-1-NAPHTHYL)PROPYL]CYCLOPROPANECARBOXAMIDE

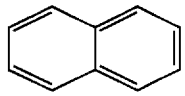

Using the procedure described in Example 1, but replacing acetyl chloride by cyclopropanecarbonyl chloride, the compound of the title is obtained.

Characteristics:
Molar mass: 283.37 g/mol for $C_{18}H_{21}NO_2$
Meltling point: 121°–123° C.
Recrystallization solvent: cyclohexane
Yield: 92%
Elution solvent: acetone/toluene/cyclohexane (4:4:2)
Rf: 0.59

Elemental analysis:

|  | C % | H % | O % | N % |
| --- | --- | --- | --- | --- |
| Calculated | 76.30 | 7.47 | 11.29 | 4.94 |
| Found | 76.25 | 7.93 | 11.19 | 4.85 |

Infrared spectroscopic analysis: 3280 cm$^{-1}$: vNH (amide) 3050–2800 cm$^{-1}$: vCH (alkyl) 1620 cm$^{-1}$: vCO (amide) 1590 cm$^{-1}$: vC=C (aromatic) 1250 cm$^{-1}$: vOCH$_3$ Proton NMR spectroscopic analysis (DMSO-d$_6$, δ, 300 MHz):
0.58–0.70 ppm (unresolved complex, 4H): H$_{g,h}$
1.55 ppm (multiplet, 1H): H$_f$
1.81 ppm (multiplet, 2H): H$_c$
3.00 ppm (triplet, 2H): H$_b$ J$_{b-c}$=7.67 Hz
3.16 ppm (multiplet, 2H): H$_d$
3.93 ppm (singlet, 3H): H$_a$
7.14–7.36 ppm (unresolved complex, 4H): H$_{2,3,6,8}$
7.70 ppm (doublet, 1 H): H$_4$ J$_{ortho}$=7.90 Hz
7.84 ppm (doublet, 1 H): H$_5$ J$_{ortho}$=8.95 Hz
8.19 ppm (signal, 1 H): H$_e$

EXAMPLE 3: N-[3-(7-METHOXY-1-NAPHTHYL) PROPYL]PENTANAMIDE

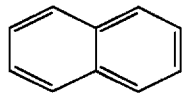

Using the procedure described in Example 1, but replacing acetyl chloride by pentanoyl chloride, the compound of the title is obtained.
Characteristics:
Molar mass: 299.41 g/mol for C$_9$H$_{25}$NO$_2$
Melting point: 75°–76° C.
Recrystallization solvent: cyclohexane
Yield: 56%
Elution solvent: acetone/toluene/cyclohexane (4:4:2)
Rf: 0.57
Elemental analysis:

|  | C % | H % | O % | N % |
| --- | --- | --- | --- | --- |
| Calculated | 76.22 | 8.42 | 10.69 | 4.68 |
| Found | 75.90 | 8.81 | 10.59 | 4.57 |

Infrared spectroscopic analysis:
3280 cm$^{-1}$: vNH (amide)
3040–2800 cm$^{-1}$: vCH (alkyls)
1620 cm$^{-1}$: vCO (amide)
1590 cm$^{-1}$: vC=C (aromatic)
1250 cm$^{-1}$: vOCH$_3$
Proton NMR spectroscopic analysis (DMSO-d$_6$, δ, 300 MHz):
0.87 ppm (triplet, 3H): H$_i$ J$_{i-h}$=7.29 Hz
1.26 ppm (multiplet, 2H): H$_h$
1.50 ppm (multiplet, 2H): H$_g$
1.81 ppm (multiplet, 2H): H$_c$
2.09 ppm (triplet, 2H): H$_f$ J$_{f-g}$=7.39 Hz
3.00 ppm (triplet, 2H): H$_b$ J$_{b-c}$=7.68 Hz
3.16 ppm (multiplet, 2H): H$_d$
3.93 ppm (singlet, 3H): H$_a$
7.16–7.35 ppm (unresolved complex, 4H): H$_{2,3,6,8}$
7.70 ppm (doublet, 1 H): H$_4$ J$_{ortho}$=7.83 Hz
7.83 ppm (doublet, 1H): H$_5$ J$_{ortho}$=8.94 Hz
7.90 ppm (signal, 1H): H$_e$

EXAMPLE 4: N-PROPYL-N'-[3-(7-METHOXY-1-NAPHTHYL)PROPYL]UREA

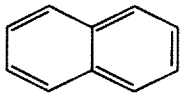

Starting from the amine of Preparation 1 as in Example 1, but reacting with propyl isocyanate instead of acetyl chloride, the compound of the title is obtained.
Melting point: 121° C.

EXAMPLES 5 TO 19

Using the procedure described in Example 1, but replacing acetyl chloride by the appropriate acyl chloride, the compounds of the following examples are obtained:

EXAMPLE 5: N-[3-(7-METHOXY-1-NAPHTHYL) PROPYL]PROPIONAMIDE

EXAMPLE 6: N-[3-(7-METHOXY-1-NAPHTHYL) PROPYL]BUTANAMIDE

EXAMPLE 7: N-[3-(7-METHOXY-1-NAPHTHYL) PROPYL]HEXANAMIDE

EXAMPLE 8: N-[3-(7-METHOXY-1-NAPHTHYL) PROPYL]HEPTANAMIDE

EXAMPLE 9: N-[3-(7-METHOXY-1-NAPHTHYL) PROPYL]ISOPROPYLCARBOXAMIDE

EXAMPLE 10: N-[3-(7-METHOXY-1-NAPHTHYL)PROPYL]BROMOACETAMIDE

EXAMPLE 11: N-[3-(7-METHOXY-1-NAPHTHYL)PROPYL] CYCLOBUTANECARBOXAMIDE

EXAMPLE 12: N-[3-(7-METHOXY-1-NAPHTHYL)PROPYL] CYCLOPENTANECARBOXAMIDE

EXAMPLE 13: N-[3-(7-METHOXY-1-NAPHTHYL)PROPYL]CYCLOHEXANE CARBOXAMIDE

EXAMPLE 14: N-3-(7-METHOXY-1-NAPHTHYL)PROPYL] CYCLOPROPYLACETAMIDE

EXAMPLE 15: N-[3-(7-METHOXY-1-NAPHTHYL)PROPYL] CYCLOBUTYLACETAMIDE

EXAMPLE 16: N-[3-(7-METHOXY-1-NAPHTHYL)PROPYL]VINYLCARBOXAMIDE

EXAMPLE 17: N-[3-(7-METHOXY-1-NAPHTHYL)PROPYL]ALLYLCARBOXAMIDE

EXAMPLE 18: N-[3-(7-METHOXY-1-NAPHTHYL)PROPYL] PROPARGYLCARBOXAMIDE

EXAMPLE 19: N-[3-(7-METHOXY-1-NAPHTHYL)PROPYL]CROTYLCARBOXAMIDE

EXAMPLES 20 TO 24:

Using the procedure described in Example 4, but replacing propyl isocyanate by the appropriate alkyl isocyanate, the following compounds are obtained.

EXAMPLE 20: N-METHYL-N'-[3-(7-METHOXY-1-NAPHTHYL)PROPYL]UREA

EXAMPLE 21: N-ETHYL-N'-[3-(7-METHOXY-1-NAPHTHYL)PROPYL]UREA

EXAMPLE 22: N-BUTYL-N'-[3-(7-METHOXY-1-NAPHTHYL)PROPYL]UREA

EXAMPLE 23: N-PENTYL-N'-[3-(7-METHOXY-1-NAPHTHYL)PROPYL]UREA

EXAMPLE 24: N-CYCLOPROPYL-N'-[3-(7-METHOXY-1-NAPHTHYL)PROPYL]UREA

EXAMPLES 25 TO 27:

The compounds of the Examples 1, 2 and 3 are reacted with Lawesson's reagent so as to obtain, respectively, the compounds of the following examples:

EXAMPLE 25: N-[3-(7-METHOXY-1-NAPHTHYL)PROPYL]THIOACETAMIDE

EXAMPLE 26: N-[3-(7-METHOXY-1-NAPHTHYL)PROPYL]CYCLOPROPANETHIOCARBOXAMIDE

EXAMPLE 27: N-[3-(7-METHOXY-1-NAPHTHYL)PROPYL]THIOPENTANAMIDE

EXAMPLES 28 TO 30:

Using the procedure described in Example 4, but replacing propyl isocyanate by the appropriate alkyl isothiocyanate, the following products are obtained:

EXAMPLE 28: N-METHYL-N'-[3-(7-METHOXY-1-NAPHTHYL)PROPYL]THIOUREA

EXAMPLE 29: N-ETHYL-N'-[3-(7-METHOXY-1-NAPHTHYL)PROPYL]THIOUREA

EXAMPLE 30: N-PROPYL-N'-[3-(7-METHOXY-1-NAPHTHYL)PROPYL]THIOUREA

EXAMPLE 31: N-METHYL-N'-[3-(7-METHOXY-1-NAPHTHYL)PROPYL]ACETAMIDE

Using the procedure described in Example 1, but starting from N-methyl-N-[3-(7-methoxy-1-naphthyl)propyl]amine (Preparation 16), the compound of the title is obtained.

EXAMPLES 32 TO 38:

Using the procedure described in Example 1, but starting from the appropriate 3-(7-alkoxy-1-naphthyl)propylamine obtained in Preparations 17 to 23, the following products are obtained, respectively:

EXAMPLE 32: N-[3-(7-ETHOXY-1-NAPHTHYL)PROPYL]ACETAMIDE

EXAMPLE 33: N-[3-(7-PROPOXY-1-NAPHTHYL)PROPYL]ACETAMIDE

EXAMPLE 34: N-[3-(7-BUTYLOXY-1-NAPHTHYL)PROPYL]ACETAMIDE

EXAMPLE 35: N-[3-(7-PENTOXY-1-NAPHTHYL)PROPYL]ACETAMIDE

EXAMPLE 36: N-[3-(7-HEXYLOXY-1-NAPHTHYL)PROPYL]ACETAMIDE

EXAMPLE 37: N-[3-(7-CYCLOHEXYLOXY-1-NAPHTHYL)PROPYL]ACETAMIDE

EXAMPLE 38: N-[3-(7-CYCLOPROPYLMETHOXY-1-NAPHTHYL)PROPYL]ACETAMIDE

EXAMPLES 39 TO 44:

Using the procedure described in Example 1, but starting from the appropriate 3-(7-alkyl-1-naphthyl)propylamine obtained in Preparations 24 to 29, the following products are obtained, respectively:

EXAMPLE 39: N-[3-(7-METHYL-1-NAPHTHYL)PROPYL]ACETAMIDE

EXAMPLE 40: N-[3-(7-ETHYL-1-NAPHTHYL)PROPYL]ACETAMIDE

EXAMPLE 41: N-[3-(7-PROPYL-1-NAPHTHYL)PROPYL]ACETAMIDE

EXAMPLE 42: N-[3-(7-BUTYL-1-NAPHTHYL)PROPYL]ACETAMIDE

EXAMPLE 43: N-[3-(7-PENTYL-1-NAPHTHYL)PROPYL]ACETAMIDE

EXAMPLE 44: N-[3-(7-HEXYL-1-NAPHTHYL)PROPYL]ACETAMIDE

EXAMPLES 45 TO 56:

Using the procedure described in Example 1, but starting from the compounds of Preparations 2 to 13, the following products are obtained, respectively:

EXAMPLE 45: N-[3-(7-ETHYL-1,2,3,4-TETRAHYDRO-1-NAPHTHYL)PROPYL]ACETAMIDE

EXAMPLE 46: N-[3-(5-ETHYLBENZOTHIOPHEN-3-YL)PROPYL]ACETAMIDE

EXAMPLE 47: N-[3-(7-M ETHYL-1,2,3,4-TETRAHYDRO-1-NAPHTHYL)PROPYL]ACETAMIDE

EXAMPLE 48: N-[3-(7-PROPYL-1,2,3,4-TETRAHYDRO-1-NAPHTHYL)PROPYL]ACETAMIDE

EXAMPLE 49: N-[3-(7-BUTYL-1,2,3,4-TETRAHYDRO-1-NAPHTHYL)PROPYL]ACETAMIDE

EXAMPLE 50: N-[3-(5-METHYLBENZOFURAN-3-YL)PROPYL]ACETAMIDE

EXAMPLE 51: N-[3-(5-ETHYLBENZOFURAN-3-YL)PROPYL]ACETAMIDE

EXAMPLE 52: N-[3-(7-METHOXY-1,2,3,4-TETRAHYDRO-1-NAPHTHYL)PROPYL]ACETAMIDE

EXAMPLE 53: N-[3-(5-METHOXYBENZOFURAN-3-YL)PROPYL]ACETAMIDE

EXAMPLE 54: N-[3-(1-NAPHTHYL)PROPYL]ACETAMIDE

EXAMPLE 55: N-[3-(5-METHOXYBENZOTHIOPHEN-3-YL)PROPYL]ACETAMIDE

EXAMPLE 56: N-[3-(5-METHOXY-3-INDOLYL)PROPYL]ACETAMIDE

EXAMPLE 57: N-[3-(5-METHYLBENZOTHIOPHEN-3-YL)PROPYL]CYCLOPROPANE CARBOXAMIDE

Using the procedure described in Example 2, but starting from the compound obtained in Preparation 14, the product of the title is obtained.

EXAMPLES 58 AND 59:

Using the procedure described in Example 4, but starting from the compounds of Preparations 2 and 3, the following products are obtained, respectively:

EXAMPLE 58: N-PROPYL-N'-[3-(7-ETHYL-1,2,3,4-TETRAHYDRO-1-NAPHTHYL) PROPYL] UREA

EXAMPLE 59: N-PROPYL-N'-[3-(5-ETHYLBENZOTHIOPHEN-3-YL)PROPYL]UREA

EXAMPLES 60 TO 63:

Using the procedure described in Examples 1 to 4, but starting from the compound obtained in Preparation 15, the following products are obtained, respectively:

EXAMPLE 60: N-[4-(7-METHOXY-1-NAPHTHYL)BUTYL]ACETAMIDE

EXAMPLE 61: N-[4-(7-METHOXY-1-NAPHTHYL)BUTYL]CYCLOPROPANE CARBOXAMIDE

EXAMPLE 62: N-[4-(7-METHOXY-1-NAPHTHYL)BUTYL]PENTANAMIDE

EXAMPLE 63: N- PROPYL-N'-[4-(7-METHOXY-1-NAPHTHYL)BUTYL]UREA

EXAMPLE 64: N-[6-(7-METHOXY-1-NAPHTHYL)HEXYL]ACETAMIDE

Using the procedure described in Example 1, but starting from the compound obtained in Preparation 30, the product of the title is obtained.

EXAMPLE 65: N-[3-(7-METHOXY-3-BENZOYL-1-NAPHTHYL)PROPYL]ACETAMIDE

By reacting N-[3-(7-methoxy-1-naphthyl)propyl] acetamide obtained in Example 1 with benzoyl chloride, the compound of the title is obtained.

EXAMPLE 66: N-[3-(7-METHOXY-3-BENZYL-1-NAPHTHYL)PROPYL]ACETAMIDE

On reducing the compound of Example 65 with mercury and zinc, the compound of the title is obtained.

EXAMPLE 67: N-[3-(7-METHOXY-3-ACETYL-1-NAPHTHYL)PROPYL]ACETAMIDE

By reacting N-[3-(7-methoxy-1-naphthyl)propyl] acetamide obtained in Example 1 with acetyl chloride, the compound of the title is obtained.

EXAMPLE 68: N-[3-(7-METHOXY-3-ETHYL-1-NAPHTHYL)PROPYL]ACETAMIDE

On reducing the compound of Example 67 with mercury and zinc, the compound of the title is obtained.

PHARMACOLOGICAL STUDY

EXAMPLE A: STUDY OF ACUTE TOXICITY

The acute toxicity was assessed after oral administration to groups of 8 mice (26±2 grams). The animals were observed at regular intervals during the first day and daily during the two weeks following treatment. The $LD_{50}$, bringing about the death of 50% of the animals, was evaluated.

The $LD_{50}$ of the test products is greater than 1000 mg.kg$^{-1}$ for most of the compounds studied, indicating the low toxicity of the compounds of the invention.

EXAMPLE B: STUDY OF BINDING TO MELATONIN RECEPTORS

B1) STUDY ON SHEEP PARS TUBERALIS CELLS

Studies of binding of the compounds of the invention to melatonin receptors were carried out according to standard techniques on sheep pars tuberalis cells. The pars tuberalis of the adenohypophysis is, in effect, characterized in mammals by a high density of melatonin receptors (Journal of Neuroendocrinology vol. (1), pp. 1–4 (1989)).

PROTOCOL

1) Membranes of sheep pars tuberalis are prepared and used as target tissue in saturation experiments to determine the binding affinities and capacities for [2-$^{125}$I] iodomelatonin.

2) Membranes of sheep pars tuberalis are used as target tissue with the different test compounds in experiments of competitive binding relative to [2-$^{125}$I]iodomelatonin.

Each experiment is carried out in triplicate, and a series of different concentrations is tested for each compound.

After statistical treatment, the results enable the binding affinities of the test compound to be determined.

RESULTS

It is apparent that the compounds of the invention possess a potent affinity for melatonin receptors, this being higher than that of melatonin itself.

B2) STUDY ON CHICK (*GALLUS DOMESTICUS*) BRAIN CELL MEMBRANES

The animals used are 12-day-old chicks (*Gallus domesticus*). They are sacrificed between 1 pm and 5 pm on the day of their arrival. The brains are rapidly removed and frozen at -200° C., and are then stored at -80° C. The membranes are prepared according to the method described by Yuan and Pang (Journal of Endocrinology 128, pages 475–482, 1991). [$^{125}$I]Melatonin is incubated in the presence of the membranes in a solution buffered to pH 7.4 for 60 min at 25° C. At the end of this period, the membrane suspension is filtered (Whatman GF/C). The radioactivity retained on the filter is determined using a Beckman® LS 6000 liquid scintillation counter.

The products used are:

[2-$^{125}$I]iodomelatonin melatonin standard products novel substances

In primary screening, the substances are tested at 2 concentrations ($10^{-7}$ and $10^{-5}$M). Each result is the mean of 3 independent measurements. The active substances selected on the basis of the primary screening results were subjected to a quantitative determination of their efficacy ($IC_{50}$). They are used at 10 different concentrations.

Thus the $IC_{50}$ values found for the preferred compounds of the invention, which correspond to the affinity values, show that the binding of the test compounds is very strong.

EXAMPLE C: FOUR PLATES TEST

The products of the invention are administered via the esophagus to groups of ten mice. One group receives acacia syrup. 30 minutes after administration of the products under study, the animals are placed in compartments whose floor is composed of four metal plates. Every time the animal passes from one plate to another, it receives a mild electric shock (0.35 mA). The number of transits is recorded over one minute. After administration, the compounds of the invention significantly increase the number of transits, demonstrating the anxiolytic activity of the compounds of the invention.

EXAMPLE D: COMPOUNDS OF THE INVENTION ON THE CIRCADIAN RHYTHMS OF LOCOMOTOR ACTIVITY IN RATS

The involvement of melatonin in driving, by day/night alternation, the majority of the physiological, biochemical and behavioral circadian rhythms has enabled a pharmacological model to be established for the investigation of melatoninergic ligands.

The effects of the substances are tested on a large number of parameters, and especially on the circadian rhythms of locomotor activity which represent a reliable marker of the activity of the endogenous circadian clock.

In this study, the effects of such substances on a particular experimental model, namely the rat placed in temporal isolation (permanent darkness), are evaluated.

EXPERIMENTAL PROTOCOL

One-month-old male Long Evans rats are subjected from the time of their arrival at the laboratory to an illumination cycle of 12 h of light per 24 h (LD 12:12).

After 2 to 3 weeks of adaptation, they are placed in cages equipped with a wheel connected to a recording system so as to detect the phases of locomotor activity and thus to monitor the nycthemeral (LD) or circadian (DD) rhythms.

As soon as it is apparent that the recorded rhythms are being driven in a stable manner by the LD 12:12 illumination cycle, the rats are placed in permanent darkness (DD).

Two to three weeks later, when the unimpeded course of natural behavior (rhythm reflecting that of the endogenous clock) is clearly established, the rats receive a daily administration of the test substance.

The observations are made by means of visualization of the rhythms of activity:

driving of the rhythms of activity by the rhythm of illumination, disappearance of the driving of the rhythms in permanent darkness, driving by the daily administration of the substance; transient or lasting effect.

A software permits:

measurement of the duration and intensity of activity, and the period of the rhythm in animals whose natural behavior is unimpeded and during treatment, the demonstration, where appropriate, by spectral analysis, of the existence of circadian and non-circadian (for example ultradian) components.

RESULTS:

It is clearly apparent that the compounds of the invention enable a powerful action on the circadian rhythm to be obtained via the melatoninergic system.

EXAMPLE E: ANTI-ARRHYTHMIC ACTIVITY

PROTOCOL:

(Ref: LAWSON J.W. et al. J. Pharmacol. Expert. Therap. 1968, 160, pp. 22-31)

The test substance is administered intraperitoneally to a group of 3 mice 30 min before exposure to chloroform anesthesia. The animals are then observed for 15 min. The absence of recording of arrhythmias and of heart rates above 200 beats/min (control: 400–480 beats/min) in two animals at least indicates a significant protection.

EXAMPLE F: PHARMACEUTICAL COMPOSITION: TABLETS 1000 tablets containing a 5 mg dose of N-[3-(7-methoxy-1-naphthyl)propyl]acetamide N-[3-(7-Methoxy-1-naphthyl)propyl]acetamide 5 g
Wheat starch: 20 g
Corn starch: 20 g
Lactose: 30 g
Magnesium stearate: 2 g
Silica: 1 g
Hydroxypropylcellulose: 2 g

We claim:

1. A compound selected from the group consisting of those of formula (I):

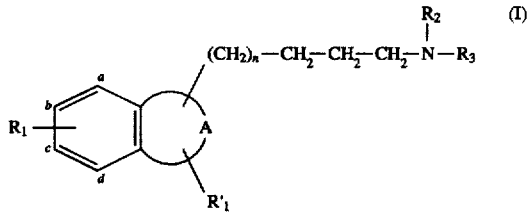

in which:

$R_1$ represents hydrogen, hydroxyl, a radical $R_6$, or a group —O—$R_6$, $R_6$ being selected from the group consisting of alkyl, substituted alkyl, cycloalkyl, substituted cycloalkyl, cycloalkylalkyl, substituted cycloalkylalkyl, alkenyl, alkynyl, cycloalkenyl, phenyl, substituted phenyl, phenylalkyl, substituted phenylalkyl, dicycloalkylalkyl, substituted dicycloalkylalkyl, diphenylalkyl, and substituted diphenylalkyl, $R'_1$ is selected from the group consisting of hydrogen, halogen, $R'_6$, —O—$R'_6$, —OH, —CO—$R_7$, —$CH_2$—$R_7$, and —O—CO—$R_7$, $R'_6$ being selected from the group consisting of the same meanings as $R_6$, which is as defined above, the radicals $R_6$ and $R'_6$ being identical or different, $R_7$ represents a radical selected from the group consisting of $(C_1-C_5)$alkyl, substituted $(C_1-C_5)$alkyl, cycloalkyl, substituted cycloalkyl, cycloalkyl$(C_1-C_5)$alkyl, substituted cycloalkyl$(C_1-C_5)$alkyl, phenyl, substituted phenyl, phenyl$(C_1-C_5)$alkyl, and substituted phenyl $(C_1-C_5)$alkyl, A, with the benzene ring to which it is linked, forms a cyclic group selected from the group consisting of tetrahydronaphthalene, dihydronaphthalene, naphthalene, benzothiophene, 2,3-dihydrobenzothiophene, benzofuran, 2,3-dihydrobenzofuran, indole, and indoline, n represents zero, 1, 2, or 3, $R_2$ represents hydrogen or alkyl, $R_3$ represents:

a group of formula $(R_{32})$:

with X' representing sulfur or oxygen and $R_5$ representing hydrogen or a radical selected from the group consisting of alkyl, substituted alkyl, cycloalkyl, substituted cycloalkyl, cycloalkylalkyl, and substituted cycloalkylalkyl, its enantiomers and diastereoisomers, and an addition salt thereof with a pharmaceutically-acceptable base.

2. A compound of claim 1 having a selection from those consisting of formula (1) to (12),

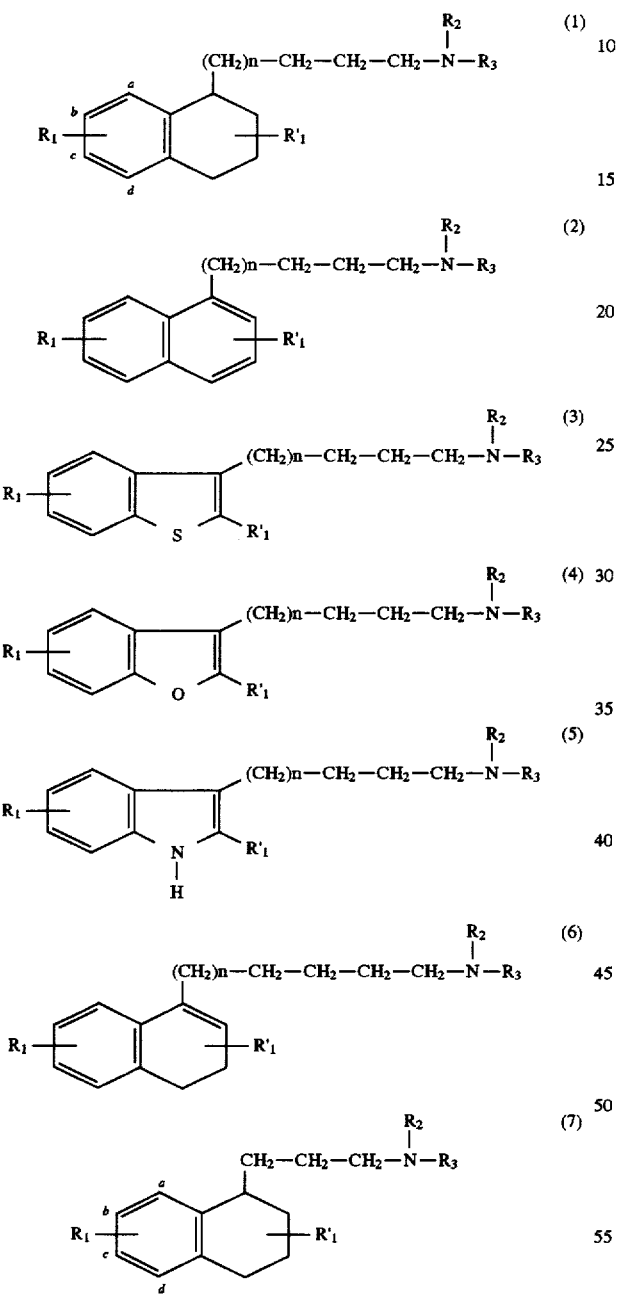

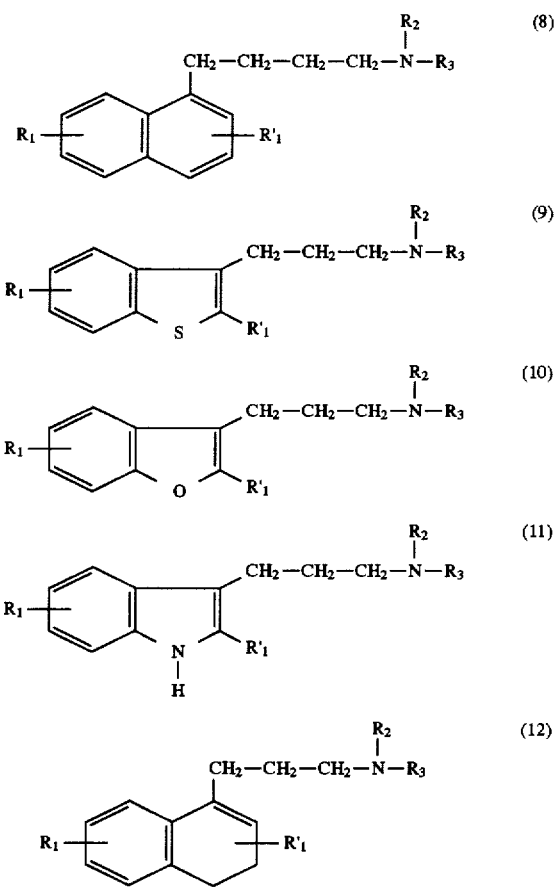

in which $R_1$, $R'_1$, $R_2$, $R_3$ and n are as defined in claim 1.

3. A compound of claim 1 in which $R'_1$ is a hydrogen.

4. A compound of claim 1, which is N-propyl-N'-[3-(7-methoxy-1-naphthyl)propyl]urea.

5. A pharmaceutical composition containing a compound claim 1 in combination with one or more pharmaceutically-acceptable excipients.

6. A method of treating a mammal afflicted with a disorder of the melatoninergic system comprising the step of administering to the mammal an amount of a compound of claim 1 which is effective to alleviate the said disorder.

7. A method of treating a mammal afflicted with a sleep disorder comprising the step of administering to the mammal an amount of a compound of claim 1 which is effective to alleviate the said disorder.

* * * * *

UNITED STATES PATENT AND TRADEMARK OFFICE
CERTIFICATE OF CORRECTION

PATENT NO. : 5,760,071
DATED : June 2, 1998
INVENTOR(S) : D. Lesieur, V. Leclerc, P. Depreux, P. Delagrange, P. Renard Page 1 of 5

It is certified that error appears in the above-indentified patent and that said Letters Patent is hereby corrected as shown below:

Column 7, line 31 (approx.): "formula (IIa)" should read -- formula (IIIa) --.

Column 7, line 64: "R'$^1$," should read -- R'$_1$, --.

Column 8, line 39: Delete "[5]" from the end of the line.

Column 8, line 54: Delete "I10" from the end of the line.

Column 9, line 67: "(III/e):" at the end of the line, should read -- (II/e): --.

Column 10, line 11: "(II/g):" at the end of the line, should read -- (II/f): --.

Column 11, line 30: "Formula (i)," should read -- Formula (I), --.

Column 11, line 48 (approx.): "Formula (VII):" should read -- Formula (VIII) --.

Column 12, line 25: In the first line of the formula, "R$^1$" should read -- R' --.

Column 14, line 21: "(9.5 Gm$^3$)" should read: -- (9.5 cm$^3$) --.

UNITED STATES PATENT AND TRADEMARK OFFICE
CERTIFICATE OF CORRECTION

PATENT NO. : 5,760,071
DATED : June 2, 1998  Page 2 of 5
INVENTOR(S) : D. Lesieur, V. Leclerc, P. Depreux, P. Delagrange, P. Renard It is certified that error appears in the above-indentified patent and that said Letters Patent is hereby corrected as shown below:

Column 16, line 1: "acetoneltoluene/cyclohexane" should read: -- acetone/toluene/cyclohexane --.

Column 16, line 50: "950 strength alcohol" should read: -- 95° strength alcohol --.

Column 17, line 20: "6.75 cm3" should read -- 6.75 cm$^3$ --.

Column 17, line 67: "60 088 mol" should read: -- 0.088 mol --.

Column 18, line 3: "3 3.34g" at the beginning of the line, should read -- 3.34g --.

Column 18, line 6: Delete "T10" after the word "acetate".

Column 18, line 18: "acetone/toluenelcyclohexane" should read: -- acetone/toluene/cyclohexane --.

Column 18, line 36: "$H_{b\ jb-c}$=7.10 Hz" should read -- $H_b\ J_{b-c}$=7.10 Hz --.

Column 18, line 38: "H,$J_{c-b}$=7.10 Hz" should read -- $H_c\ J_{c-b}$=7.10 Hz --.

UNITED STATES PATENT AND TRADEMARK OFFICE
CERTIFICATE OF CORRECTION

PATENT NO. : 5,760,071
DATED : June 2, 1998  Page 3 of 5
INVENTOR(S) : D. Lesieur, V. Leclerc, P. Depreux, P. Delagrange, P. Renard It is certified that error appears in the above-indentified patent and that said Letters Patent is hereby corrected as shown below:

Column 18, line 40: Delete "10" from the beginning of the line.

Column 18, line 55: "(3.3 cmi)" at the end of the line should read -- (3.3 cm$^3$) --.

Column 18, line 56: "cm3" at the end of the line should read -- cm$^3$ --.

Column 19, line 18 (appeox.): "1620 and 1590 cm⁻:" should read -- 1620 and 1590 cm$^{-1}$: --.

Column 21, line 9: "H$_4$ 1 J $_{ortho}$=7.78 Hz" should read -- H$_4$ J$_{ortho}$=7.78 Hz --.

Column 21, line 52: "2960-2920 cm: v alkyl CH" should read: -- 2960-2920 cm$^{-1}$ v alkyl CH --.

Column 21, line 61: "CH$_2$(c) J$_c$=6.60 Hz" should read -- CH$_2$(c) J$_{c-d}$=6.60 Hz --.

Column 24, line 45: Insert -- : -- after the word "solvent".

Column 24, line 64: Delete "15" from the beginning of the line.

UNITED STATES PATENT AND TRADEMARK OFFICE
CERTIFICATE OF CORRECTION

PATENT NO. : 5,760,071
DATED : June 2, 1998
INVENTOR(S) : D. Lesieur, V. Leclerc, P. Depreux, P. Delagrange, P. Renard It is certified that error appears in the above-indentified patent and that said Letters Patent is hereby corrected as shown below:

Column 25, line 16: "-50°C," should read -- -5°C,--.

Column 25, line 45: Delete "20" from the beginning of the line.

C0lumn 26, line 28: Delete "25" from the beginning of the line.

Column 26, line 54: "(-50° C)." should read: --(-5° C).--

Column 26, line 62: At the end of the line, "$C_{15}H_8O_4S$" should read: -- $C_{15}H_{18}O_4S$ --.

Column 28, line 6: "$H_a$ $J_{ortho}$=8.91 Hz" should read: -- $H_6$ $J_{ortho}$=8.91 Hz --.

Column 31, line 36: "$C_9H_{25}NO_2$" should read: -- $C_{19}H_{25}NO_2$ --.

Column 34, line 31: "EXAMPLE 47: N-[3-(7-M ETHYL .. " should read: -- EXAMPLE 47: N-[3-(7-METHYL... --

Column 39. line 45: Delete the last "$CH_2$" in Formula (6).

UNITED STATES PATENT AND TRADEMARK OFFICE
CERTIFICATE OF CORRECTION

PATENT NO. : 5,760,071
DATED : June 2, 1998
INVENTOR(S) : D. Lesieur, V. Leclerc, P. Depreux, P. Delagrange, P. Renard It is certified that error appears in the above-indentified patent and that said Letters Patent is hereby corrected as shown below:

Column 40, line 4: Delete the last "$CH_2$" in Formula (8).

Column 40, line 43(approx.: After the word "compound" at the end of the line, insert -- of --.

Signed and Sealed this

Twenty-seventh Day of June, 2000

Q. TODD DICKINSON

*Attest:*

*Attesting Officer*   *Director of Patents and Trademarks*